(12) United States Patent
Chatterjee et al.

(10) Patent No.: US 11,890,351 B2
(45) Date of Patent: Feb. 6, 2024

(54) CHEMOSELECTIVE RAPID AZO-COUPLING REACTION FOR BIOCONJUGATION

(71) Applicant: Trustees of Boston College, Chestnut Hill, MA (US)

(72) Inventors: Abhishek Chatterjee, Brookline, MA (US); Partha Sarathi Addy, Brighton, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 94 days.

(21) Appl. No.: 16/012,060

(22) Filed: Jun. 19, 2018

(65) Prior Publication Data

US 2018/0360984 A1 Dec. 20, 2018

Related U.S. Application Data

(60) Provisional application No. 62/522,282, filed on Jun. 20, 2017.

(51) Int. Cl.

| A61K 47/68 | (2017.01) |
|---|---|
| C07K 16/32 | (2006.01) |
| A61K 47/54 | (2017.01) |
| A61K 49/00 | (2006.01) |
| C07D 209/20 | (2006.01) |
| C07H 21/00 | (2006.01) |
| A61K 51/10 | (2006.01) |

(52) U.S. Cl.
CPC ........ *A61K 47/6851* (2017.08); *A61K 47/549* (2017.08); *A61K 47/6803* (2017.08); *A61K 49/0043* (2013.01); *A61K 49/0058* (2013.01); *A61K 51/1045* (2013.01); *C07D 209/20* (2013.01); *C07H 21/00* (2013.01); *C07K 16/32* (2013.01); *C07K 2317/24* (2013.01); *C07K 2317/55* (2013.01)

(58) Field of Classification Search
CPC .............. A61K 47/6851; A61K 47/549; A61K 47/6803; A61K 49/0043; A61K 49/0058; A61K 51/1045; C07D 209/20; C07H 21/00; C07K 16/32; C07K 2317/24; C07K 2317/55
See application file for complete search history.

(56) References Cited

U.S. PATENT DOCUMENTS 4,707,553 A * 11/1987 Satomura ............. C07D 209/08
548/440
2017/0349891 A1 12/2017 Chatterjee et al.

OTHER PUBLICATIONS

Eichler et al., Handbook of Experimental Pharmacology (1966), vol. XIX, p. 70. (Year: 1966).*

(Continued)

*Primary Examiner* — Robert S Cabral
(74) *Attorney, Agent, or Firm* — HoustonHogle LLP

(57) ABSTRACT

Novel biomolecular conjugates containing non-natural aromatic chemical moieties covalently coupled to a diazonium compound and methods of their use are disclosed.

19 Claims, 23 Drawing Sheets
(19 of 23 Drawing Sheet(s) Filed in Color)

(56) References Cited

OTHER PUBLICATIONS

Zhang et al., PNAS, vol. 101, No. 24 (2004), 8882-8887 (Year: 2004).*

Reay, University of York, Apr. 2016 (Year: 2016).*

De Graaf et al., Bioconjugate Chem. vol. 20, No. 7, 2009 1281-1295 (Year: 2009).*

Addy, P.S., et al., "A Chemoselective Rapid Azo-Coupling Reaction (CRACR) for Unclickable Bioconjugation," J. Am. Chem. Soc., 139: 11670-11673 (2017).

Bruckman, M.A., et al., "Surface modification of tobacco mosaic virus with "click" chemistry," ChemBioChem., 9(4): 519-523 (2008).

Gavrilyuk, J., et al., "Formylbenzene diazonium hexafluorophosphate reagent for tyrosine-selective modification of proteins and the introduction of a bioorthogonal aldehyde," Bioconjugate chemistry, 23 (12): 2321-2328 (2012).

He, J., et al., "A Photobasic Functional Group," J. Am. Chem. Soc., 137(31): 9764-9767 (2015).

Hooker, J.M., et al., "Interior surface modification of bacteriophage MS2," J. Am. Chem. Soc., 126: 3718-3719 (2004).

Italia, J. S., et al., "An orthogonalized platform for genetic code expansion in both bacteria and eukaryotes," Nat. Chem. Biol., 13 (4): 446-450 (2017).

Jensen, S.M., et al., "Light-Activated Triazabutadienes for the Modification of a Viral Surface," Chembiochem, 17, 2216-2219 (2016).

Kimani, F.W., and Jewett, J.C., "Water-soluble triazabutadienes that release diazonium species upon protonation under physiologically relevant conditions," Angew. Chem. Int. Ed., 54 (13): 4051-4054 (2015).

Schlick, T.L., et al., "Dual-surface modification of the tobacco mosaic virus," J. Am. Chem. Soc., 127: 3718-3723 (2005).

Osgood, et al., "An Efficient Opal-Suppressor Tryptophanyl Pair Creates New Routes for Simultaneously Incorporating up to Three Distinct Noncanonical Amino Acids into Proteins in Mammalian Cells", Agnew. Chem. Int. Ed. 2023, 62, e202219269, Apr. 12, 2023, 43 Pages.

Reay, et al., "Unified Mild Reaction Conditions For C2-Selective Pd-Catalysed Tryptophan Arylation, Including Tryptophan-Containing Peptides", Organic & Biomolecular Chemistry, Jun. 25, 2015, 13 Pages.

Eichler et al., Handbook of Experimental Pharmacology (1966), vol. XIX: Chapter 2: Chemical Analysis of Indolealkylamines and Related Compounds by Arne Hanson; pp. 66-112.

Italia, J .S. et al., "Mutually Orthogonal Nonsense-Suppression Systems and Conjugation Chemistries for Precise Protein Labeling at up to Three Distinct Sites," JACS, 141:6204-6212 (2019).

Yuda, C., et al., "Creation of Bacterial Cells with 5-Hydroxytryptophan as a 21st Amino Acid Building Block," Chem, 6:2717-2727 (2020).

* cited by examiner

FIG. 1A
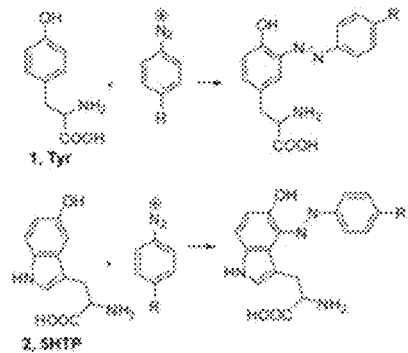
FIG. 1C
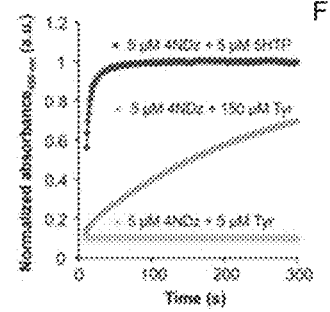
FIG. 1B
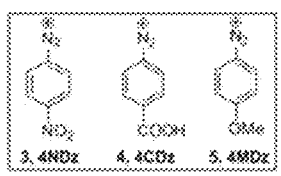
FIG. 1D
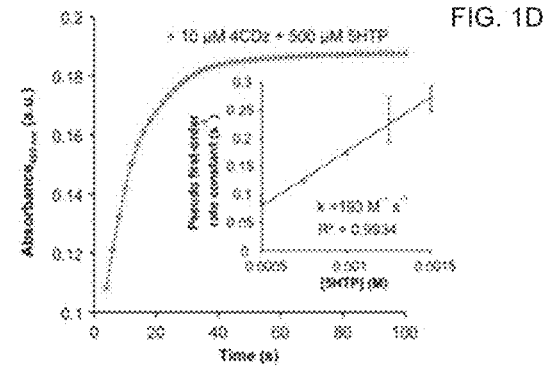
FIG. 1E
FIG. 2A
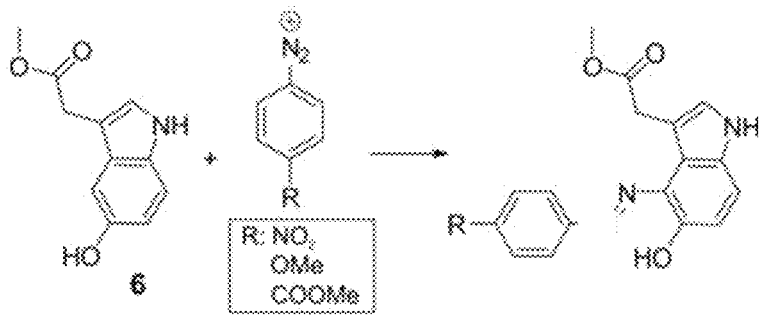
FIG. 2B
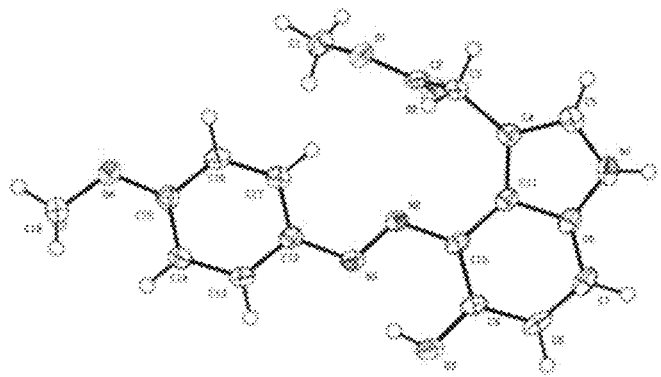

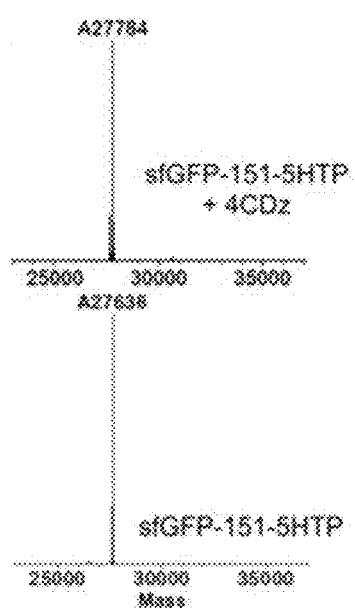
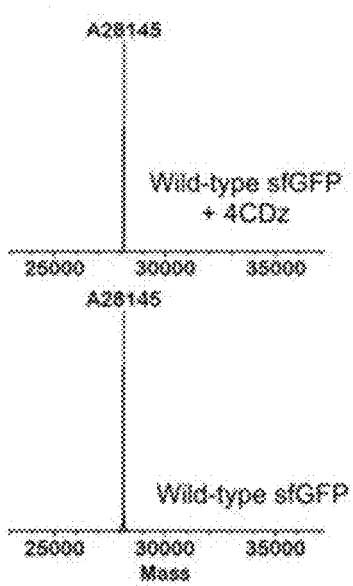
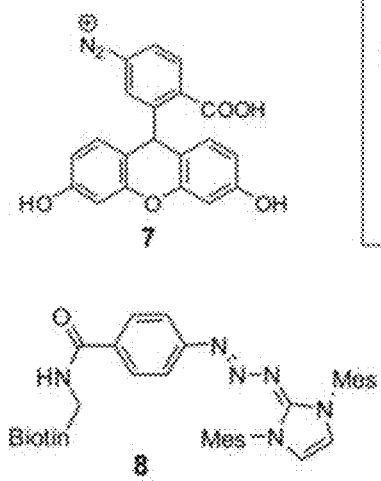
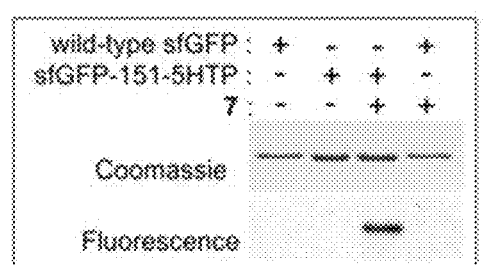
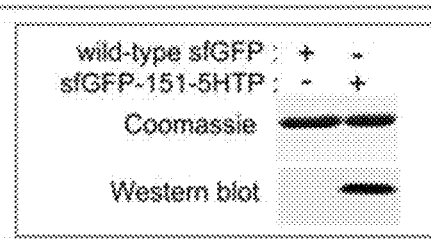
FIG. 3

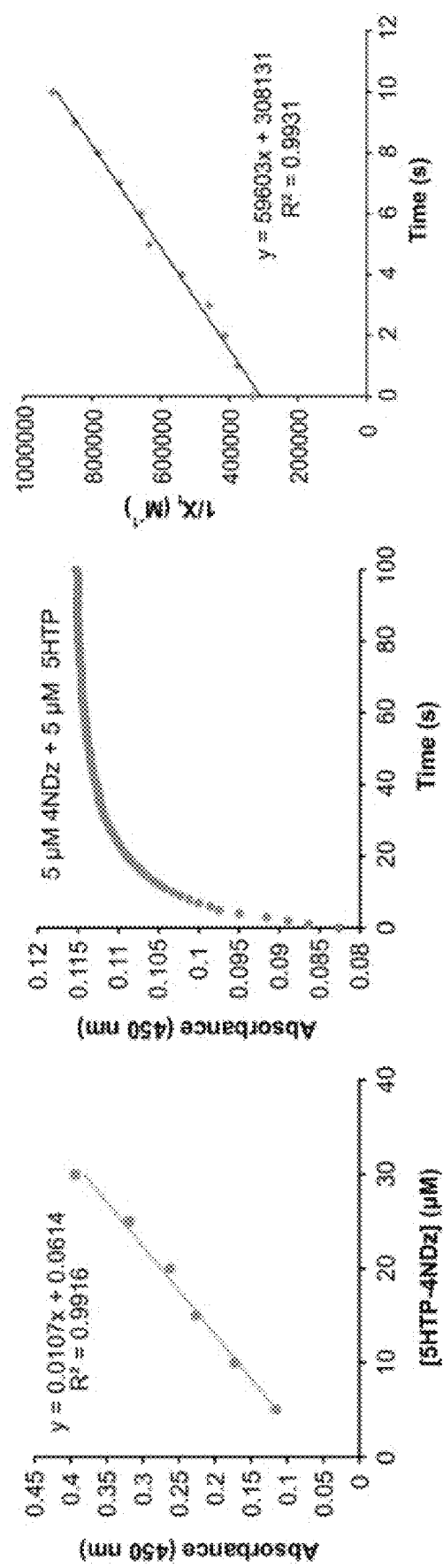

FIG. 12A
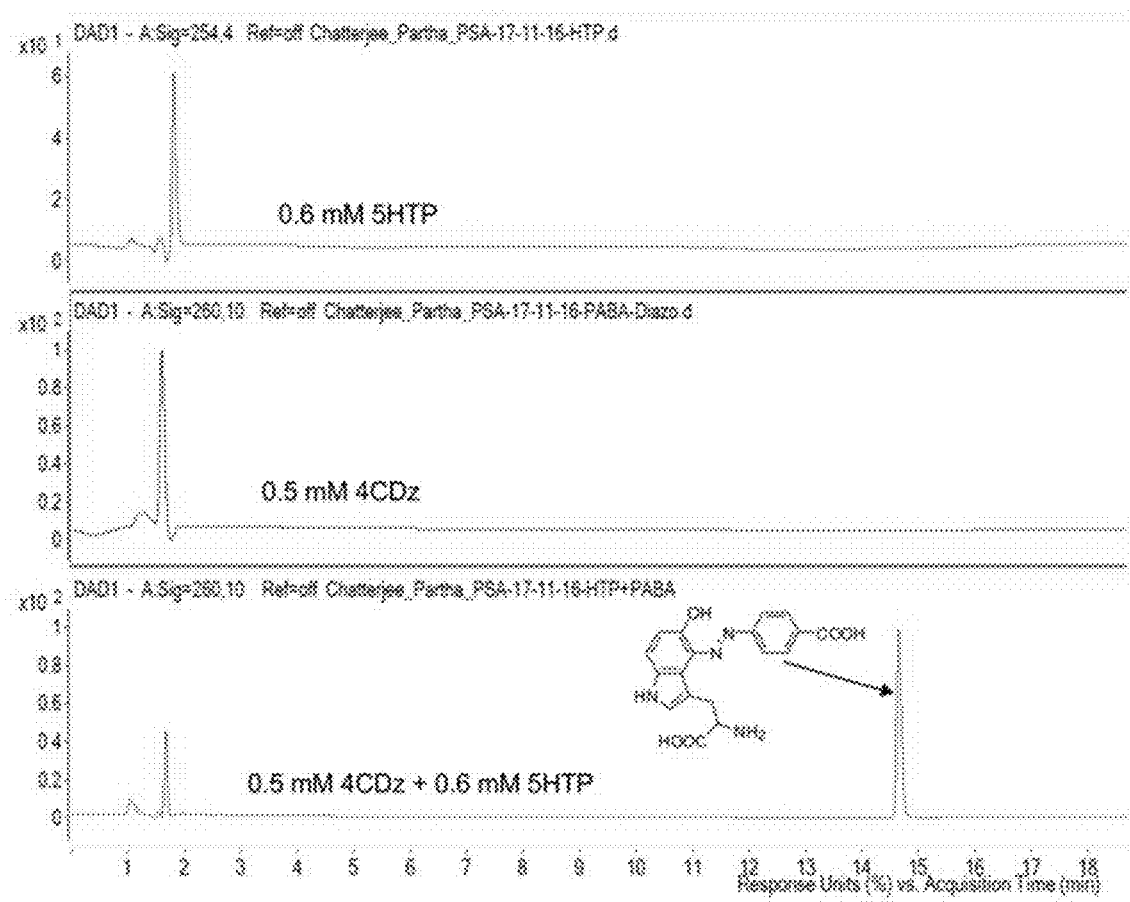
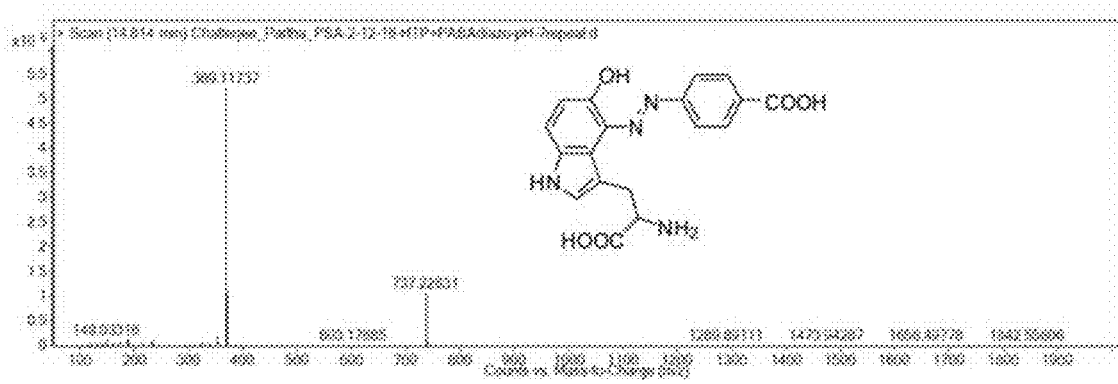
FIG. 12B

CHEMOSELECTIVE RAPID AZO-COUPLING REACTION FOR BIOCONJUGATION

RELATED APPLICATIONS

This application claims the benefit under 35 USC 119(e) of U.S. Provisional Application No. 62/522,282 filed on Jun. 20, 2017, which is incorporated herein by reference in its entirety.

FIELD OF THE INVENTION

The present invention is directed to a novel bioconjugation strategy using a chemoselective rapid azo-coupling reaction.

BACKGROUND OF THE INVENTION

The ability to chemoselectively label complex biomolecules has emerged as a powerful strategy to both study and engineer their structure and function. To achieve this, uniquely reactive non-natural chemical functionalities are incorporated into biomolecules through synthetic or biosynthetic routes, followed by their selective functionalization using a bioorthogonal reaction. A variety of such bioorthogonal reactions have been developed to date, including the condensation between an aldehyde/ketone and an alkoxyamine/hydrazine, the Staudinger ligation, the Cu(I)-catalyzed and strain promoted cycloaddition between alkynes and azides, the inverse electron demand Diels-Aider reactions between tetrazines and strained alkenes, various 1,3-dipolar cycloadditions, etc. Many of these chemistries have been harnessed within a growing collection of genetically encoded non-canonical amino acids (ncAAs). Development of engineered nonsense-suppressing aminoacyl-tRNA synthetase (aaRS)/tRNA pairs that selectively charge such ncAAs has enabled their facile site-specific incorporation into proteins expressed in living cells, which can be subsequently used to precisely attach a variety of entities, from biophysical probes to therapeutic agents. However, many of the available conjugation chemistries are limited by their slow kinetics, the need for toxic catalysts, or a lack of compatibility with other chemistries to allow the simultaneous attachment of multiple distinct entities at different sites. Consequently, there is continued interest in additional genetically encoded chemical functionalities that can be rapidly and chemoselectively labeled using catalyst-free conjugation reactions, and that are also compatible with other available bioorthogonal chemistries to allow concurrent labeling at multiple sites.

SUMMARY OF THE INVENTION

As described herein, the present invention encompasses a chemoselective, rapid azo-coupling reaction (referred to herein as "CRACR") for bioconjugation. More specifically, encompassed by the present invention is a biomolecular conjugate comprising a biomolecule comprising one, or more, non-natural aromatic chemical moieties incorporated into the biomolecule in a site-specific manner, wherein the aromatic moiety is covalently coupled to a diazonium compound/group. The biomolecule can be any suitable biomolecule, and in particular can be a protein, polypeptide or peptide. In a specific embodiment of the present invention, the protein is an antibody, or an antibody fragment, such as an Fab fragment. The biomolecule can also encompass a nucleic acid, such as DNA or RNA.

The biomolecule of the conjugate described herein comprises one, or more, non-natural aromatic chemical moieties that is/are reactive with, and can be functionalized by, aromatic diazonium groups. These reactive, non-natural aromatic chemical moieties are typically introduced into the biomolecule in a site-specific manner using methods knows to those of skill in the art. Further, the methods described herein, and specifically taught in U.S. application Ser. No. 15/609,900 published as US2017/0349891 A1 (the teachings of which are specifically incorporated herein by reference it its entirety), are particularly useful for introducing these moieties in a site-specific manner. One of skill in the art is aware of other suitable methods for site-specific incorporation of chemical moieties into a biomolecule. The non-natural aromatic chemical moiety is preferably an electron-rich aromatic chemical moiety, thereby facilitating the reaction with the diazonium group or ion. More specifically, the chemical moiety comprises a hydroxyl-indole group; an amino-indole group; an aminophenol group; or a hydroxyl-phenol group.

In one embodiment of the present invention, the non-natural aromatic chemical moiety comprises an electron rich aromatic amino acid, or an amino acid analog. More specifically, the amino acid is selected from the group consisting of: amino-tryptophan; amino-tyrosine; hydroxyl tyrosine and histidine-imidazole, wherein the amino acids comprise electron donating substitutions.

In another embodiment of the present invention, the non-natural aromatic chemical moiety comprises a 5-hydroxyindole group, and in particular, the aromatic moiety is 5-hydroxytryptophan (5HTP), or an analog thereof. In yet another embodiment of the present invention, a 5-aminoindole group, and specifically encompasses 5-aminotyrtophan, or an analog thereof.

The biomolecular conjugate of the present invention comprises a diazonium compound that is reactive with the non-natural aromatic chemical moiety incorporated into the biomolecule. In particular, the diazonium compound (also referred to herein as a diazonium group, or a diazonium ion) is typically an aromatic diazonium compound, and more specifically is an aryl diazonium compound. In one embodiment of the present invention, the aryl diazonium compound is selected from the group consisting of: 4-nitorbenzenediazonium (4NDz); 4-carboxybenzenediazonium (4NCDz) or 4-methoxybenzenediazonium (4MCDz).

The diazonium compound of the biomolecular conjugate can itself be modified in any manner that does not interfere with its reactivity with the non-natural aromatic chemical moiety of the biomolecule, or other desired chemical reactions. For example, in one embodiment of the present invention, the diazonium compound can be labeled in a detectable manner. That is, the detectably labeled diazonium compound of the present invention can comprise a label such as a chemical dye or a fluorophore. Additionally the label can be a reactive molecule that in itself can further bind to (or react with) a binding partner. Such labels can include, for example, biotin or an enzyme. Further, the label can encompass a radioisotope for detection. Such labels can be used, for example, to follow the biomolecular conjugate during an in vitro or in vivo biological process, such as locating a specific cell type, or accumulation in a tumor. Additional examples of suitable labels are known to those of skill in the art.

In another embodiment of the present invention, the diazonium compound is modified with, or linked to, a small organic molecule, a therapeutic drug, polyethylene glycol (PEG), a nucleic acid, a protein, a polypeptide, a peptide or a biophysical probe.

In yet another embodiment of the present invention, the diazinium compound can be modified to be immobilized, or adsorbed, on a solid matrix, surface or support. More specifically, the solid support can be a bead or sphere and in particular, can be a magnetic particle or a nanopartide.

As described herein, the aromatic chemical moiety (also referred to herein as an "entity") of the biomolecule is covalently coupled to a diazonium compound via an azo-linkage. Although a very stable bond is formed, this covalent coupling between the aromatic chemical moiety and the diazonium compound is cleavable with a suitable reducing agent under suitable conditions (e.g., time, temperature, pH, diluents). Such conditions are known to those of skill in the art. In one particular embodiment, the reducing agent is dithionite. Such suitable conditions can also be determined in, for example, in tissue or tumor microenvironment for in vivo use such as for targeted drug delivery.

In a more specific embodiment of the present invention, the molecular conjugate is a labeled antibody conjugate, or antibody fragment conjugate, wherein the antibody, or antibody fragment, comprises one, or more, non-natural aromatic chemical moieties incorporated into the antibody in a site-specific manner, wherein the aromatic moiety is covalently coupled to a detectably-labeled diazonium compound. In particular, the antibody fragment is an Fab fragment, for example, wherein the Fab fragment is an Fab fragment of the anti-Her2 antibody Herceptin and the conjugate is labeled with a fluorescent label.

Also as described herein, the present invention encompasses methods of chemoselective modification of a biomolecule, wherein the biomolecule comprises one, or more, non-natural aromatic chemical moieties that are naturally occurring in the biomolecule, or that have been specifically incorporated into the biomolecule in a site-specific manner, such as described herein, and in U.S. application Ser. No. 15/609,900. The method encompasses reacting the non-natural aromatic chemical moiety with a diazonium group under conditions suitable to form an azo-linkage via an azo-coupling reaction between the aromatic chemical moiety and the diazonium group. The diazonium group is thus covalently linked to the aromatic chemical moiety, thereby modifying the biomolecule in a site-specific/chemoselective manner. The claimed methods can further comprise optionally cleaving the azo-linkage between the non-natural, aromatic chemical moiety and the diazonium group with a suitable reducing agent, thereby releasing the diazonium group from the biomolecule. As described above, the reducing agent can be, for example, dithionite. Also as described above, the diazonium group can be detectably labeled.

Another embodiment of the present invention encompasses an alternative method of chemoselective modification of a biomolecule, wherein the target biomolecule is modified by incorporating one, or more, non-natural aromatic chemical moieties into the biomolecule in a site-specific manner as described herein, and then reacting the one, or more aromatic chemical moieties with a diazonium group under conditions suitable to form an azo-linkage via an azo-coupling reaction between the aromatic chemical moiety and the diazonium group, thereby modifying the biomolecule in a chemoselective manner. This method also encompasses optionally cleaving the azo-linkage with a suitable reducing agent, thereby releasing the diazonium group from the biomolecule.

Also encompassed by the present invention are kits for the chemoselective modification of a biomolecule, wherein the biomolecule comprises one, or more, non-natural aromatic chemical moieties. In particular, the kit comprises a container containing a diazonium compound, and additional reagents necessary and suitable for azo-coupling the diazonium compound to the biomolecule. Optionally, the diazonium compound is detectably labeled. The kit can further comprise reagents suitable for use in a procedure to incorporate one, or more, non-natural aromatic chemical moieties in the biomolecule. Alternatively, the kit can comprise a biomolecular conjugate as described herein, wherein the biomoleculer conjugate is detectably labeled. More specifically, the biomolecular conjugate of the kits described herein is an antibody, or antibody fragment.

The present invention shows that the electron-rich 5-hydroxyindole can be rapidly functionalized by aromatic diazonium compounds with a high degree of chemoselectivity. The non-canonical amino acid 5-hydroxytryptophan (5HTP, 2, FIG. 1A) has been genetically encoded in both $E.$ $coli$ and eukaryotes, enabling efficient site-selective incorporation of the 5-hydroxyindole group into virtually any protein. The 5-hydroxytryptophan residue was shown to allow rapid, chemoselective protein modification using the azo-coupling reaction, and the utility of this bioconjugation strategy was further illustrated by generating a functional antibody-fluorophore conjugate. Although the resulting azo-linkage is otherwise stable, it is shown that it can be efficiently cleaved upon treatment with dithionite. The present invention establishes a unique chemoselective "unclickable" conjugation reaction to site-specifically modify proteins expressed in both bacteria and eukaryotes.

The technology of the present invention enables covalent attachment of any entity (drug, fluorophore, other biophysical probes, polyethylene glycol, other proteins, nucleic acids, a solid matrix like a solid surface), carrying a aryl-diazonium group, onto a specific site of any recombinant protein. The target protein can be expressed in any expression system ($E.$ $coli$/eukaryotic cell) site-specifically incorporating the stable and cheap amino acid 5HTP. Simple addition of the aryl-diazonium containing molecule to this protein will result in its spontaneous attachment to the 5HTP site through the rapid azo-coupling reaction. Such conjugation reactions can be used to generate 1) antibody-drug conjugates, 2) antibody-fluorophore conjugates, 3) antibody-enzyme conjugates, 4) therapeutic protein-PEG conjugate, 5) protein-nucleic acid conjugates, 6) immobilize proteins on surfaces site-specifically, 6) generate kits for site-specific modification of proteins, etc.. Synthesis of other biomolecules (e.g., DNA, RNA) with the 5-hydroxyindole will also allow their precise labeling through the azo-coupling reaction.

This conjugation chemistry is compatible with existing bioconjugation strategies, such as azide-alkyne cycloaddition and tetrazine-strained alkene reaction, and can be used together to simultaneously attach multiple different entities onto distinct sites of a target protein. Technology to site-specifically incorporate 5HTP as well as another unnatural amino acid incorporating azide/cyclopropene into any two sites of a target protein has already been developed, and shown that the two sites can be concurrently labeled with two distinct entities (e.g., two different fluorophores).

The 5HTP-azo covalent conjugate generated as a result of this coupling chemistry has many potentially useful properties. This group is a fluorescence quencher (the quenching behavior can be tuned by using different synthetic aryl-diazonium compounds), which can be used as a biophysical probe together with a fluorophore to monitor dynamic structural changes in biomolecules (e.g., conformational change or proteolysis). The azo group is also known to undergo reduction under anoxic environment (e.g., tumor microenvironment), which can be used to create antibody-drug conjugates that spontaneously and selectively release drugs in the tumor microenvironment.

The 5HTP-incorporating aminoacyl-tRNA synthetase/tRNA can also be used to substitute all tryptophan residues with 5HTP (partially) within the proteome of any cell. Subsequent chemoselective labeling of these 5HTP-residues using the aryl diazonium chemistry will enable their facile identification (e.g., through fluorophore labeling)/isolation (e.g., through biotin labeling). This provides a unique way to identify newly synthesized proteins in a cell.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. The patent or application file contains at least one drawing executed in color. Copies of this patent or patent application publication with color drawings(s) will be provided by the Office upon request and payment of the necessary fee. Of the drawings:

FIG. 1A-E shows 5HTP 2 exhibit significantly higher reactivity towards aryl diazonium ions relative to Tyr 1. A) Azo-coupling reaction of aryl-diazoniums with Tyr and 5HTP. B) Structures of aryl-diazonium ions used. C) Observed rate of azo-coupling reaction of 4NDz 3 with 5HTP and Tyr at indicated concentrations in 100 mM phosphate buffer (pH 7, room temperature). D) Measurement of the rate of the azo-coupling reaction between 4CDz and 5HTP under pseudo-first order conditions. E) Second-order rate constants of the azo-coupling reactions between the indicated partners (in $M^{-1}s^{-1}$). Each rate represents an average of three independent experiments, and error represents standard deviation.

FIG. 2A-B shows characterizing the product of the azo-coupling reaction with 5HTP. A) Products of the azo-coupling reaction between 6, a 5HTP analog, and three aryl-di azoniums were purified and characterized. B) Crystal structure of the azo-coupling product of 6 with 4MDz.

FIG. 3A-E shows chemoselective protein labeling using 5HTP-directed azo-coupling reaction. A) Incubating 10 µM sfGFP-151-5HTP with 40 µM 4CDz at room temperature for 30 minutes results in complete protein labeling (expected mass 27784. Da). B) The wild-type protein does not undergo modification upon the same treatment. C) Structures of the fluorescent diazonium compound 7, and the biotin-triazabutadiene conjugate 8, synthesized for protein labeling through CRACR D) Selective fluorescence-labeling of sfGFP-151-5HTP by 7, shown by fluorescence imaging following SDS-PAGE. E) Selective biotinylation of sfGFP-151-5HTP using photolyzed 8, revealed by western blot (using a streptavidin-HRP probe) following SDS-PAGE.

FIG. 7A-C shows evaluating the kinetic parameters of the reaction between 4NDz and 5HTP. Due to the very fast nature of this reaction, its rate could only be measured under low concentrations (<10 µM) of both reagents. To measure the kinetic parameters of this bimolecular reaction, equal concentrations of both reactants were used (5 µM each in 100 mM phosphate buffer at pH 7), where the second order rate equation reduces to $1/[X]_t=1/[X]_0+k_2t$ ($[X]_t$: concentration of either reactant at time t; $[X]_0$: initial concentration of either reactant; $k_2$: rate constant). To obtain the concentration of the product (4NDz-5HTP) at a given time from the observed absorbance at 450 nm, a standard curve was first generated (A). This was used to obtain $X_t$ from the observed increase in absorbance at 450 nm (B). Plotting $1/X_t$ against time yielded the rate constant (C). The reported value (63287±6512 $M^{-1}s^{-1}$) represents an average of three independent experiments; error represents standard deviation.

FIG. 12A-B shows HPLC-MS (ESI-TOF) analysis of the azo-coupling reactions of 4CDz with 5HTP. Indicated reactions in 100 mM phosphate buffer (pH 7) were allowed to continue at room temperature for 10 minutes, and then analyzed by HPLC-MS. HPLC traces (A) and MS scans of the azo-coupling product peaks (B) are shown.

DETAILED DESCRIPTION OF THE PREFERRED EMBODIMENTS

Figure 4A:
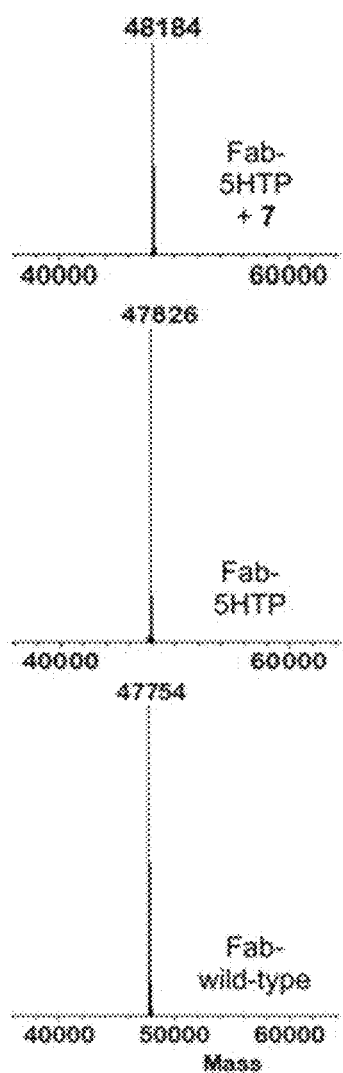
FIG. 4A-C shows a functional Herceptin-Fab-fluorophore conjugate created using 5HTP-directed CRACR, A) ESI-MS analysis of the wild-type Fab (expected mass 47752 Da), Fab-169-5HTP(expected mass 47826 Da), and the conjugate between Fab-169-5HTP and 7 (expected mass 48186 Da). B) SDS-PAGE followed by Coomassie staining (top) and fluorescence imaging (bottom) reveals selective fluorescence-labeling of Fab-169-5HTP, but not wild-type Fab by 7. C) The conjugate between 7 and Fab-169-5HTP conjugate can bind the Her2-overexpressing SK-BR-3 cells, as shown by FACS analysis. Percentage of cells fluorescing within the $R_4$ gate is shown in each case.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated liked items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Bioorthogonal chemical reporters that enable selective functionalization of complex biomolecules have become a cornerstone of chemical biology. Despite the exciting developments over the last two decades, the demand for new bioorthogonal reactions with unique abilities, and those compatible with existing chemistries for concurrent multi-site-directed labeling, remains high. The azo-coupling reaction between an aromatic diazonium ion and aromatic amino-acid residues, such as tyrosine (Tyr, 1; FIG. 1A), has been previously used to chemically modify proteins. However, the inability to achieve site-specific labeling, owing to the abundance of surface exposed tyrosine residues commonly found on proteins, significantly limits the utility of this conjugation strategy. Even though reactive diazoniums, e.g., 4-nitrobenzenediazonium (4NDz, 3, FIG. 1B), can label tyrosine residues at physiological pH, less electrophilic counterparts are only able to react at significantly elevated pH. It was anticipated that the identification of aromatic groups that exhibit enhanced reactivity towards aromatic diazonium ions could form the basis of developing a new bioorthogonal conjugation reaction. The ability to genetically encode such groups would further enable its site-specific incorporation into proteins, facilitating its use for chemoselective protein labeling.

The present disclosure establishes a unique chemoselective "unclickable" conjugation reaction to site-specifically modify proteins expressed in both bacteria and eukaryotes. The ability to precisely chemically label complex biomolecules (protein, DNA, RNA, etc.) is highly useful to understand and engineer their properties. As described herein, a new highly efficient "bioorthogonal" chemical reaction between a 5-hydroxyindole and an aromatic diazonium ion, both of which are non-natural chemical groups not found in biomolecules has been developed. As shown herein, 5-hydroxytryptophan (5HTP), a non-natural amino acid containing the 5-hydroxyindole group, can be selectively labeled by various aryl-diazonium ions in the presence of all the natural amino acids. If this amino acid residue is incorporated into proteins, it can be used for site-specific protein labeling. As described in U.S. application Ser. No. 15/609,900 a TGA stop codon suppression technology has been developed (using an engineered aminoacyl-tRNA synthetase/tRNA pair) to incorporate a 5HTP residue into any chosen site of any protein expressed in $E.$ $coli$ or eukaryotic cells (previous patent application). It is demonstrated herein that the 5HTP residue on a protein can be selectively labeled by the chemoselective azo-coupling reaction. Using this strategy, a recombinant protein was conjugated with a fluorophore, as well as a biotin group where the recombinant proteins were expressed in $E.$ $coli$ and mammalian cells with a site-specifically installed 5HTP residue. This protein labeling reaction is rapid (complete in less than 30 minutes), highly specific for the 5HTP residue, and proceeds under ambient conditions without the need for any it is demonstrated herein that it can be selectively broken upon treatment with dithionite, a protein-compatible reducing agent. The ability to chemically attach and detach molecules onto specific sites of a target protein is unique to this bioconjugation strategy Overall, the ability to 1) site-specifically incorporate 5HTP, a stable and cheap non-natural amino acid, into any protein of interest expressed in both $E.$ $coli$ and eukaryotic cells, 2) chemoselectively functionalize this non-natural residue with readily generated diazonium ions through a rapid ($10^2$-$10^4$ $M^{-1}s^{-1}$, making it one of the fastest among known bioconjugation strategies) catalyst-free azo-coupling reaction under physiological conditions, 3) systematically tune the coupling chemistry by rational substitution on the aryl-diazonium species, and 4) unclick the resulting azo linkage (if desired) using the relatively mild dithionite treatment will make this bioconjugation strategy a useful new tool for industrial protein modification needs.

As a result of this chemoselective azo-coupling reaction between 5HTP and various diazonium compounds, the ability to site-specifically incorporate 5HTP into proteins and subsequent protein labeling at this site using the reactions is now provided. The ability to simultaneously incorporate a 5HTP and another unnatural amino acid containing azide/cyclopropene residue and their subsequent concurrent labeling with two different entities using the azo-coupling chemistry and azide-alkyne click chemistry/cyclopropene-tetrazine click chemistry can also be performed.

As described herein, the feasibility of this reaction between 5HTP and three different aryl-diazonium ions has been demonstrated. However, it is reasonable that other electron rich aromatic amino acids (such as amino-tryptophan, amino-tyrosine, hydroxy-tyrosine, histidine-imidazole with electron donating substitutions) can also react selectively with aryl-diazonium ions. Additionally, a variety of other aryl diazonium compounds for their ability to functionalize 5HTP with enhanced speed and selectivity can be evaluated using the methods described herein.

Additional aryl-diazoniums can be developed, the conjugation product of which with 5HTP residue can spontaneously cleave upon the reduction of the azo-linkage under anoxic environments in vivo (e.g., tumor microenvironment).

The ability to precisely chemically label complex biomolecules (protein, DNA, RNA, etc.) is highly useful to understand and engineer their properties. To achieve this, the present invention has developed a new highly efficient "bioorthogonal" chemical reaction between a 5-hydroxyindole and an aromatic diazonium ion, both of which are non-natural chemical groups not found in biomolecules.

The present invention has further shown that 5-hydroxytryptophan (5HTP), a non-natural amino acid containing the 5-hydroxyindole group, can be selectively labeled by various aryl-diazonium ions in the presence of all the natural amino acids, suggesting if this amino acid residue is incorporated into proteins, it can be used for site-specific protein labeling. A TGA stop codon suppression technology (using an engineered aminoacyl-tRNA synthetase/tRNA pair) has been previously developed to incorporate a 5HTP residue into any chosen site of any protein expressed in $E.$ $coli$ or eukaryotic cells.

The present invention shows that the 5HTP residue on a protein can be selectively labeled by the chemoselective azo-coupling reaction. Using this strategy, a fluorophore as well as a biotin group have been conjugated onto recombinant proteins expressed in $E.$ $coli$ and mammalian cells with a site-specifically installed 5HTP residue. This protein labeling reaction is rapid (complete in less than 30 min), highly specific for the 5HTP residue, and proceeds under ambient conditions without the need for any catalyst. Even though the resulting azo bond is stable under physiological conditions, the present invention shows that it can be selectively broken upon treatment with dithionite, a protein-compatible reducing agent. The ability to chemically attach and detach molecules onto specific sites of a target protein is unique to this bioconjugation strategy.

In summary, the present invention has established a general strategy to label recombinant proteins using 5HTP-directed CRACR. The ability to 1) site-specifically incorporate 5HTP, a stable and accessible ncAA, into any protein of interest expressed in both $E.$ $coli$ and eukaryotic cells, 2) chemoselectively functionalize this non-natural residue with readily generated diazonium ions through a rapid (>190 $M^{31}$ $_1s^{-1}$ for the 4CDz scaffold) catalyst-free reaction under physiological conditions, 3) systematically tune the coupling chemistry by rational substitution on the aryl-diazonium, and 4) unclick the resulting azo-linkage (if desired) using the relatively mild dithionite treatment will make this bioconjugation strategy a useful new tool in chemical biology. It is also likely that this conjugation strategy will be compatible with existing bioorthogonal conjugation reactions (e.g., azide-alkyne click reaction)—a possibility that we are actively exploring—which will enable site-specific labeling of proteins with multiple different entities.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

EXAMPLES

The following examples are provided to illustrate embodiments of the present invention but are by no means intended to limit its scope.

The examples described herein will be understood by one of ordinary skill in the art as exemplary protocols. One of ordinary skill in the art will be able to modify the below procedures appropriately and as necessary.

Materials and Methods

All chemicals and solvents were purchased from Sigma-Aldrich or Fischer Scientific and used without further purification. In particular, 4-nitrobenzenediazonium (4NDz) and 4-methoxybenzenediazonium (4MDz) salts were purchased from Fisher chemicals. 4-carboxydiazonium tetrafluoroborate (4MDz) was synthesized starting from 4-aminobenzoic acid under standard azo-coupling conditions. Oligonucleotides for PCR were purchased from Integrated DNA technologies. PCR reactions were performed using Phusion DNA polymerase (Thermo Fisher) according to manufacturer's protocol. The DH10b strain was used for plasmid propagation and cloning purposes. Standard LB medium was used to grow bacteria either in liquid culture or Agar plates, supplemented with necessary antibiotics (95 µg/mL spectinomycin, 100 µg/mL ampicillin, 30 µg/mL kanamycin, 15 µg/mL zeocin, 10 µg/mL gentamycin). Sanger sequencing services were provided by Eton Bioscience. The ATM (Trp) $E.\ coli$ strain was used to express protein incorporating 5HTP via TGA-suppression as described previously. All HPLC-coupled mass-spectrometry analyses were performed using an Agilent Technologies 1260 Infinity ESI-TOF instrument.

Analysis azo-coupling reaction of free amino acids using HPLC-MS

Using a freshly prepared stock solution of the aryl-diazonium compound, reactions were set up in 100 mM phosphate buffer (pH 7) containing 0.5 mM of the aryl-diazonium and 0.6 mM of the amino acid. Upon the desired length of incubation at room temperature, the reactions were analyzed by HPLC-MS, A C18-reversed phase column (Phenomenex, WIDEPORE 3.6 u XB-C18, 150×2.1 mm) was used and the following gradient was used for separation (flow rate 0.2 mL/min). Mobile phase A is 0.1% formic acid in HPLC grade water and B is 0.1% formic acid in HPLC grade acetonitrile. [5% B until 0-5 min; 5%-95% linear gradient of B from 5-23 min; 95%-5% linear gradient of B from 23-28 min].

To facilitate the purification and characterization of the resulting azo-compounds, the non-polar substrates described in FIG. 2 were used. These reactions were performed in a 1:1 mixture of methanol and 100 mM aqueous phosphate buffer, followed by an ethyl acetate/water extraction to isolate the product in the organic layer.

Determining the Kinetic Parameters of Various Azo-Coupling Reactions

Figure 6:
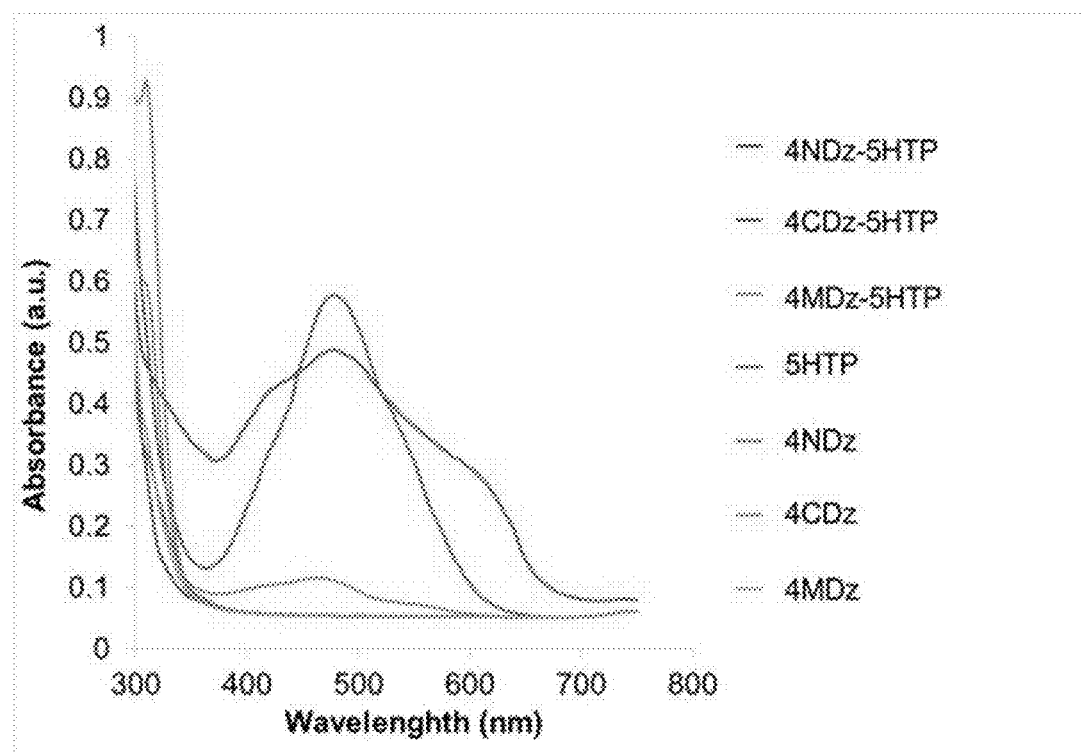
FIG. 6 shows azo conjugates, but not their precursors, uniquely absorb at 450 nm, allowing facile spectrophotometric monitoring of their formation.

As shown in FIG. 6, azo conjugates uniquely absorb at 450 nm, which was used to spectrophotometrically monitor their formation. Except for the reaction between 5HTP and 4NDz, the rates for all other reactions were measured under pseudo-first order reaction conditions, where the aryl-diazonium was used as the limiting reagent (10 µM) and varying concentrations of the amino acid was used in significant excess (at least 10-fold). Reactions were performed in 100 mM phosphate buffer (pH 7) at room temperature. Pseudo-first order rate (kB)constant for each different amino acid concentration used according to the following equation:

$$ln[A]=ln[A_0]-k_Bt$$

Plotting each pseudo-first order rate constant against the corresponding amino acid concentration yielded the second-order rate constant ($k_2$) according to the following equation:

$$kB=k_2*[B]$$

Due to the extremely rapid reaction between 4NDz and 5HTP, it was not possible to measure its rate similarly under pseudo-first order conditions. The rate of this reaction could only be measured under very low concentrations (<10 µM) of both reagents. To measure the kinetic parameters of this bimolecular reaction, equal concentrations of both reactants were used (5 µM each in 100 mM phosphate buffer a pH 7), where the second order rate equation reduces to:

$1/[X]_t=1/[X]_0+k_2t$ ($[X]_t$: concentration of either reactant at time t; [X]0: initial concentration of either reactant; $k_{2:}$ second-order rate constant).

To obtain the concentration of the product (4NDz-SHIP) at a given time from the observed absorbance at 450 nm, a standard curve was first generated (FIG. 7A). This was used to obtain $[X]_t$ from the observed increase in absorbance at 450 nm (FIG. 7B). Plotting 1/[X]t against time yielded the rate constant.

For each reaction three independent experiments were performed, and the resulting rates were averaged (associated standard deviation was reported as error).

Expression and Purification of sfGFP-151-5HTP sfGFP-151-5HTP was expressed and purified as described previously. Briefly, the ATM(Trp) $E\ coli$ strain harboring pET22b-sfGFP-151-TGA and pEvol-tac-EcTrpRS-h14 plasmids was grown in shake-flasks at 37° C. in L.B. medium to an O.D.$_{600}$ of 0.6, at which point sfGFP and EcTrpRS-h14 expression was induced by adding 1 mM each of IPTG and 5HTP. After 12 hours of protein expression at 30° C., cells were harvested and subjected to protein purification by Ni-NTA affinity chromatography. All proteins were analyzed by SDS-PAGE followed by coomassie staining, as well as by ESI mass spectrometry.

Labeling 5HTP-Residues on Proteins with 4NDz, 4CDz, and 4MDz

For 4NDz, and 4CDz, 10 µM protein in 100 mM phosphate buffer was incubated with 40 µM of aryl-diazonium compound and incubated at room temperature for 2-30 min. For 4NDz and 4CDz, complete labeling was observed in 2 min and 30 min, respectively. 4MDz was used at 250 µM for 45 min to achieve complete protein labeling. Next, free 5HTP (final concentration 200 µM) was added to quench the unreacted diazonium. The protein was desalted by repeated dilution with 100 mM phosphate buffer, followed by concentration using a concentrator (10 kDa molecular weight cutoff, Amicon Ultra-0.5 mL, centrifugal filters). Concentration of the desalted protein was adjusted back to 10 µM, followed by ESI-MS and SDS-PAGE analysis.

Fluorescein-Labeling of Proteins using CRACR

Preparation of fluorescein-diazonium (7): 6-aminofluorescein was dissolved in 10 mM MCl at a concentration of 10 mM. Separately a 60 mM sodium nitrite solution was prepared and both solutions were cooled on ice. 20 µL NaNO2 (60 mM) was added to 100 µL of fluorescein (10 mM) and vortexed for 10 sec then kept on ice to generate a 8.3 mM fluorescein diazonium solution. This solution was further diluted to 1 mM with water and used for the labeling studies.

Fluorescein-labeling protocol: 10 µL of 10 µM protein in 100 mM phosphate buffer was incubated on ice with 150 µM of 7 for 10 min. Next, 2 µl of 6 mM 5HTP was added to quench the unreacted diazonium. The protein was desalted by repeated dilution with 100 mM phosphate buffer, followed by concentration using a concentrator (10 kDa molecular weight cutoff, Amicon Ultra-0.5 mL, centrifugal filters). Concentration of the desalted protein was adjusted back to 10 µM, followed by ESI-MS and SDS-PAGE analysis.

Biotinylation of proteins with photolyzed 8

Figure 23:
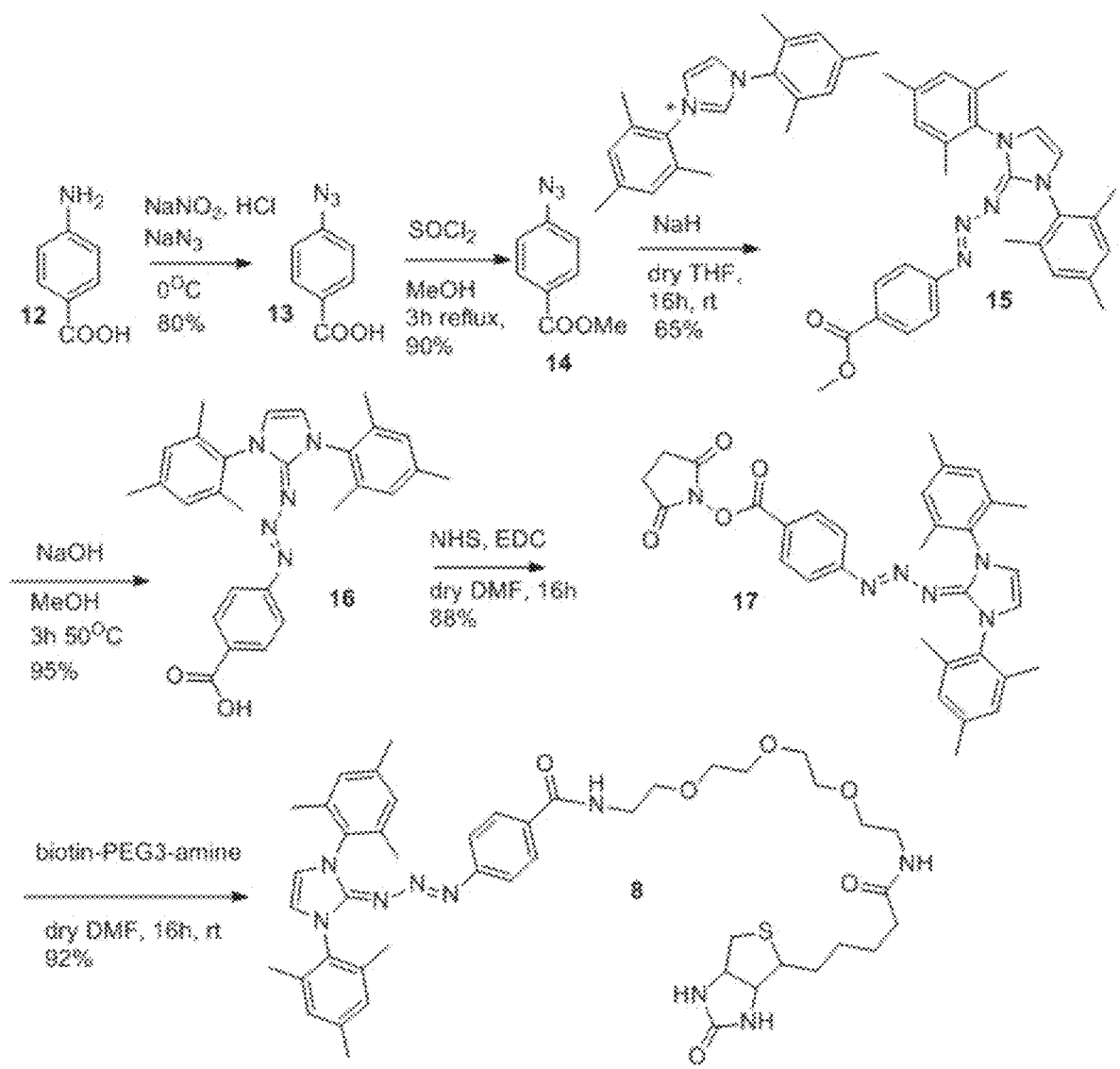
FIG. 23 shows the synthesis of compound 8.

Compound 8 was synthesized as described in FIG. 23.

8 was photolyzed for 10 s using a 120 W LED-array that emits at 365 nm (Larson Electronics), in which time the conversion of the triazabutadiene to diazonium was confirmed to be complete. 10 µM protein in 100 mM phosphate buffer (pH 7) was incubated with 150 µM of freshly photolyzed 8 for 15 min on ice, followed by the addition of 5HTP (1 mM) to quench the unreacted diazonium. The protein was desalted by repeated dilution with 100 mM phosphate buffer, followed by concentration using a concentrator (10 kDa molecular weight cutoff, Amicon Ultra-0.5 mL, centrifugal filters). Concentration of the desalted protein was adjusted back to 10 µM, followed by ESI-MS and SDS-PAGE analysis.

Dithionite-Cleavage of the Azo-Conjugate between sfGFP-151-5HTP and Photolyzed 8

The biotinylated protein, prepared as described above was desalted into 0.5 mM phosphate buffer, and its concentration was adjusted to 10 µM. 2 µL of freshly prepared dithionite (1.2 M stock solution; the final concentration 200 mM) was added to 10 µL of 10 µM biotinylated protein and incubated for 30 min at room temperature (22° C.), followed by SDS-PAGE and western blot analysis.

Anti-Biotin Western Blot

12% SDS-PAGE gels were used to resolve proteins, which were transferred from the gel to a PVDF membrane (Life Technologies) using a Trans-Blot Turbo Transfer System 15 (Bio-Rad). After transferring, the membrane was blocked with blocking solution [BSA in PBS (Thermo Scientific)] overnight at 4° C. with gentle agitation. On the next day, blocking solution was removed, and membrane was incubated with Streptavidin-HRP (Pierce; at 1:2500 dilution) for 2 hours in fresh blocking solution with gentle shaking at room temperature. The membrane was washed 7 times (10-minute incubation with agitation) with wash solution (0.1% Tween 20 in TBS. The membrane was developed using SuperSignal West Dura Kit (Fisher Scientific) and incubated for 2 minutes before signal detection by the ChemiDoc MP imaging system (BioRad).

Figure 24B:
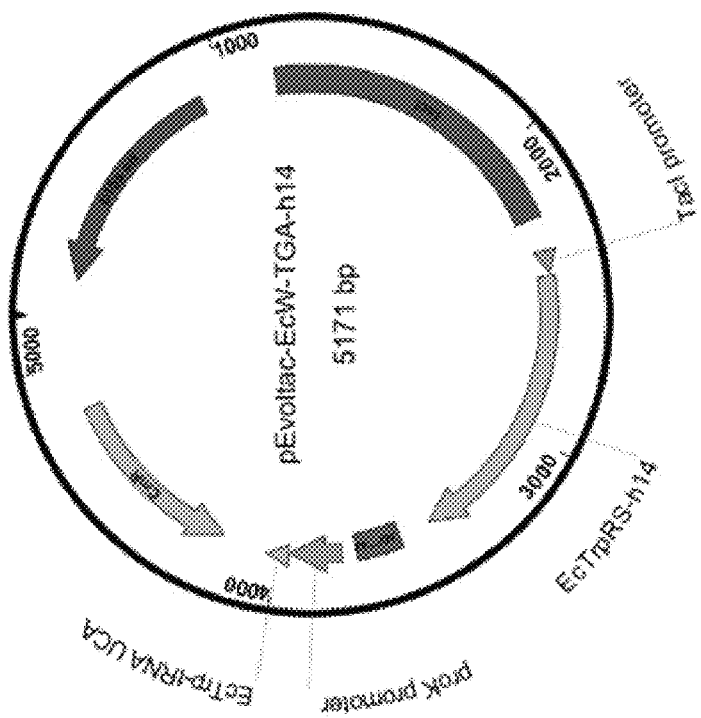
FIG. 24A-B depicts the plasmid maps of pHBK-aHer2-FAB (A) and pEvoltac-ECW-TGA-h14(B).
Figure 24A:
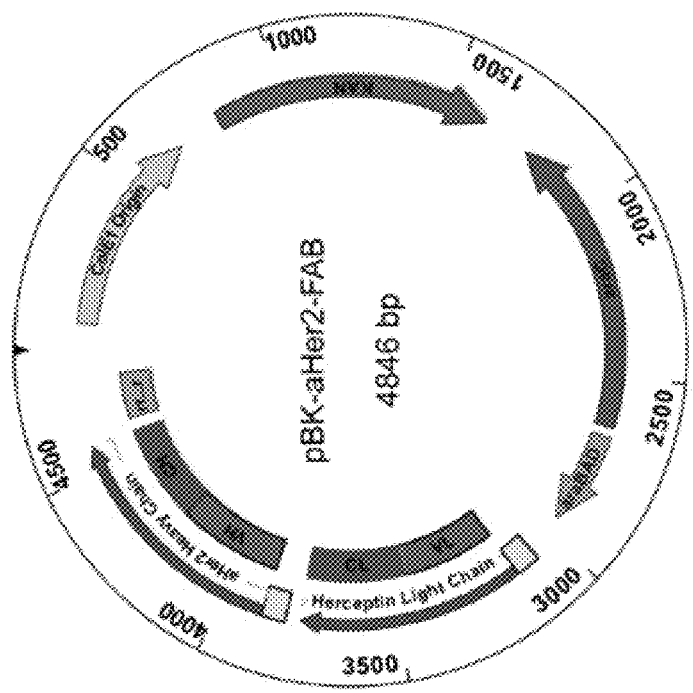

Map of pHBK-aHer2-FAB (FIG. 24A), the plasmid that was used for expression of Herceptin FAB. The previously described pEvoltac-ECW-TGA-h14 (FIG. 24B) contains the EcTrpRS-h14 and tRNAUCAEcTrp. These plasmids were co-transformed into ATMW1 strain as described in US2017/0349891, the teachings of which are incorporated herein by reference in their entirety.

Antibody Purification

Herceptin-FAB sequence was obtained from literature and cloned into a pBK vector behind the STII secretion signal. A TGA stop codon was introduced into the Fab at site K169 in the light chain using site-directed mutagenesis. pBK-aHer2-K169TGA was co-transformed with pEvolltac-EcW-5HTP, which encode EcTrpRS-h14/tRNAUCAEcTrp pair that can specifically charge 5HTP in response to TGA in the recently developedATMW1 E coli strain. The cells were grown in LB supplemented with 35 µg/mL chloramphenicol, 10 µg/mL kanamycin, 100 µg/mL spectinomycin. Upon reaching an $OD_{600}$ of 0.6, protein expression was induced with 0.02% arabinose and 1 mM IPTG 1 mM 5HTP (Chem Impex International, Inc.) was added to the media. Cells were allowed to grow for 16 hours at 30° C. in shake flasks, harvested by centrifugation, and resuspended in a periplasmic lysis buffer (20% sucrose, 30 nM Tris, pH 8, 1 mM EDTA, 0.2 mg/mL lysozyme, and Halt protease inhibitor) for 30 minutes at 37° C. Lysate was then diluted 1:1 with binding buffer (50 mM NaOAc, pH 5.2) and clarified by centrifugation at 1700 rpm for 30 minutes. Herceptin-FAB was then purified using Pierce Protein G agarose according to the manufacturer's instructions.

Antibody Labelling

4 µM Fab in 0.1 M glycine (pH 2.8) was neutralized using 1 M Tris-HCl (pH 8) buffer, and incubated with 80 µM of freshly prepared 7 on ice for 15 min; then, the excess 7 was quenched by adding 5HTP to a final concentration of 0.5 mM. The labeled antibody was dialyzed overnight against 1× PBS buffer at 4° C., and used for SDS-PAGE, ESI-MS and FACS analysis.

Cell Culture

Adherent SK-BR-3 cell lines were purchased from ATCC and grown in DMEM-high glucose (HyClone) supplemented with 100 U/mL, penicillin/streptomycin (HyClone) and 10% fetal bovine serum (FBS; Corning). They were maintained at 37° C. (humidified) and 5% $CO_2$.

Association of Fluorescein-Labeled Anti-Her2 Fab to SK-BR-3 Cells

Upon reaching confluency, SK-BR-3 cells were detached from dish using 0.25% trypsin (HyClone) for 2 minutes at 37° C. Trypsin was quenched with ice-cold DMEM supplemented with 10% FBS, and the cells were washed once with ice-cold DMEM+10% FBS, centrifuged at 2,000×g for 5 minutes, and re-suspended in ice-cold PBS. Fluorescein-labeled Herceptin-Fab (as prepared above) was added to SK-BR-3 cells at 4° C. with gentle agitation for one hour. Cells were washed once using PBS, re-suspended in cold PBS, and then analyzed by flow cytometry using a Bio-Rad S3e cell sorter. All flow cytometry plots were generated in ProSort (Bio-Rad).

Synthesis of Various Compounds

Synthesis of 4CDZ, 4

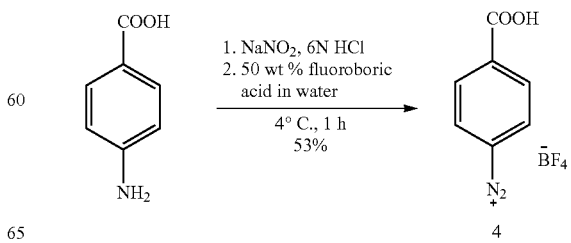

A solution of 4-aminobenzoic acid (1 gm, 7.3 mmol) in 10 mL 6 N HCl was kept on ice for 15 min. To this, a solution of sodium nitrite (590 mg, 8.75 mmol) was added and stirred for 30 min on ice. After 30 min, 10 mL 50 wt % fluoroboric acid in water was added to it and stirred for another 30 min on ice. A yellowish precipitate appeared which was filtered and dried on vacuum. 0.92 g pure product was obtained. Yield 53%; $^1$H NMR: $^1$H NMR (600 MHz, DMSO-$d_6$) δ 8.82-8.66 (m, 2H), 8.40 (d,=8.9 Hz, 2H); $^{13}$C NMR (151 MHz, DMSO-$d_6$) δ 165.59, 141.49, 133.87, 132.09, 120.54; $^{19}$F NMR (565 MHz, DMSO-$d_6$) −148.33; $^{11}$B NMR (192 MHz, DMSO-$d_6$): 1.33; ESI-MS (m/z): [M]$^+$ Calculated for $C_7H_5N_2O_2{}^+$ 149.0346 found 149.0340.

Figure 8B:
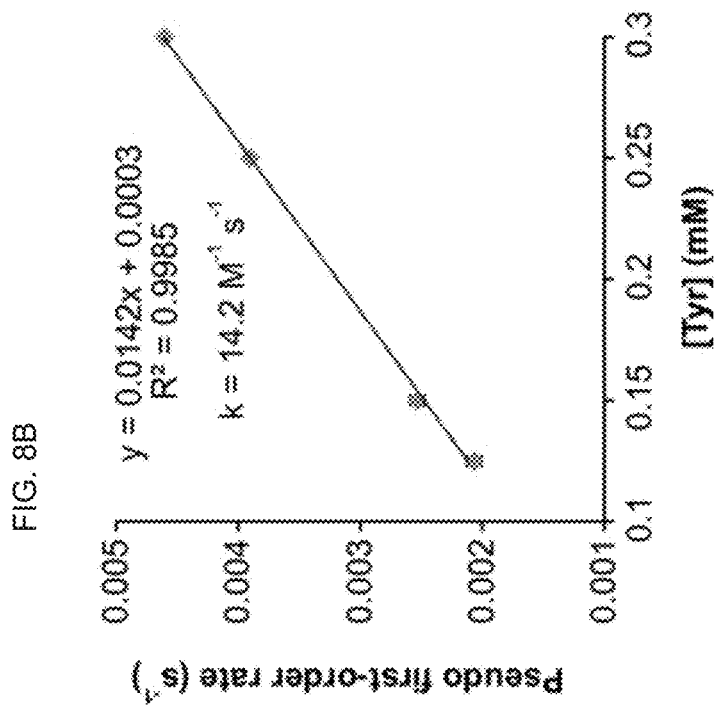
FIG. 8A-B shows evaluating the kinetic parameters of the reaction between 4NDz and tyrosine. Rate of product formation was measured under pseudo-first order conditions, where 10 µM 4NDz was mixed with an excess of tyrosine (0.1-0.3 mM) in 100 mM phosphate buffer at pH 7. A representative example is shown (A). The second-order rate constant was obtained by plotting the pseudo first-order rates against the concentration of tyrosine used (B). The reported value (14.2±0.1 $M^{-1}s^{-1}$) represents an average of three independent experiments; error represents standard deviation.
Figure 8A:
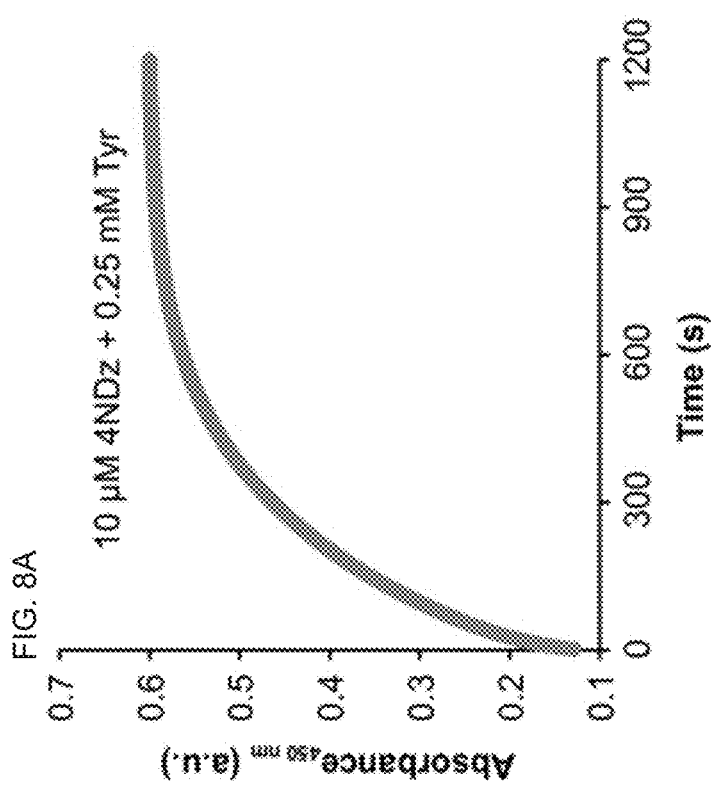
Figure 9A:
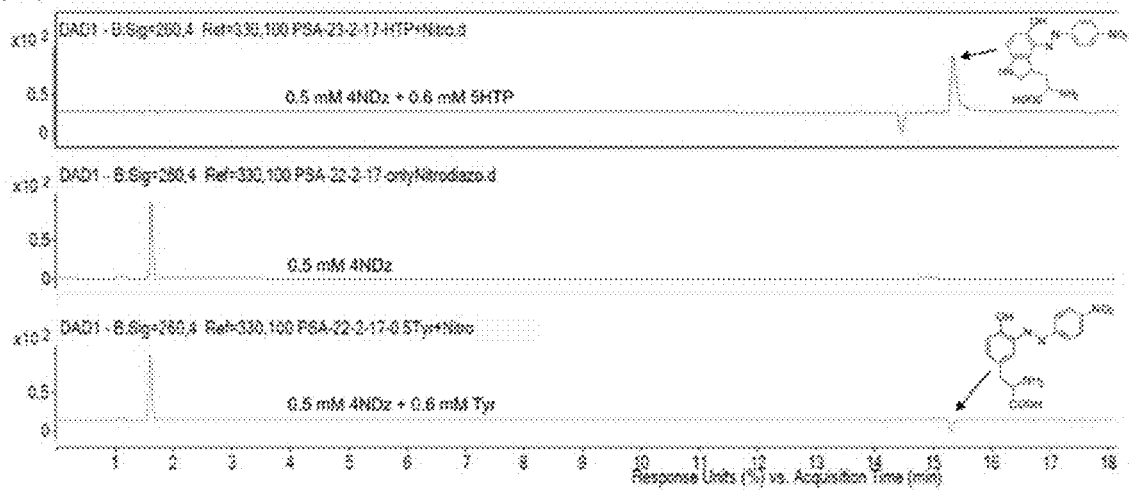
FIG. 9A-C shows HPLC-MS (ESI-TOF) analysis of the azo-coupling reactions of 4NDz with 5HTP and Tyr. Indicated reactions were allowed to continue at room temperature for 10 minutes; and then analyzed by HPLC-MS. HPLC traces (A) and MS scans of the azo-coupling product peaks (B and C) are shown.
Figure 9B:
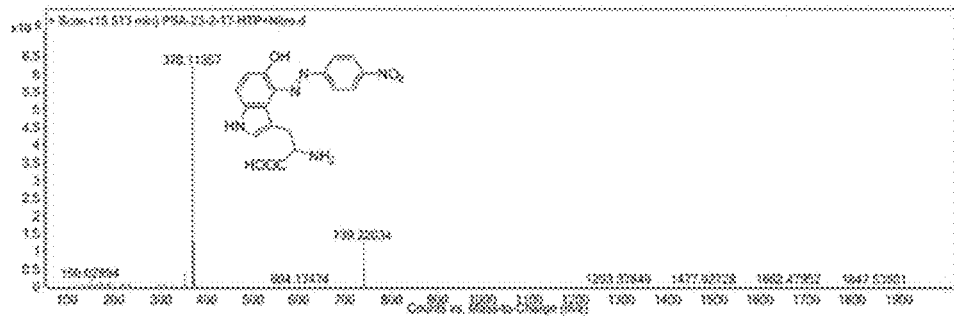
Figure 9C:
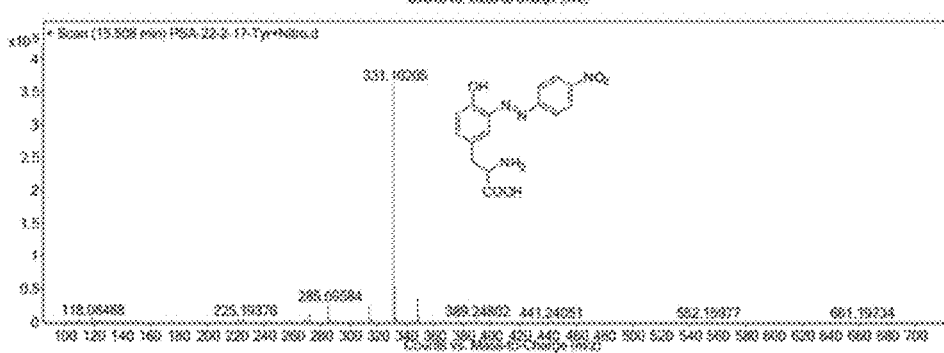

5-hydroxytryptophan (5HTP, 2; FIG. 1A) is a stable non-toxic amino acid which is widely accessible as an over-the-counter dietary supplement. It is also generated in vivo at low levels as a metabolic precursor to neurotransmitters serotonin and melatonin. The 5-hydroxyindole ring of 5HTP is highly electron rich, as indicated by its propensity to undergo oxidation under relatively mild conditions. To evaluate if the electron-rich 5-hydroxyindole exhibits enhanced reactivity towards aromatic diazonium ions, the kinetics of the azo-coupling reaction between 4NDz with 5HTP was monitored, and compared to the corresponding reaction with tyrosine under ambient conditions, in an aqueous phosphate buffer at pH 7. The formation of the chromophoric azo-coupling product in each case was monitored using spectrophotometry (increased absorption at 450 nm; FIG. 6). 5HTP was found to react with 4NDz at a rate ($k_2$=63287±6512 $M^{-1}s^{-1}$; FIG. 7, 9) approximately 4500 fold faster than tyrosine ($k_2$=14.2±0.1 $M^{-1}s^{-1}$; FIG. 8, 9). The reaction between 5 μM each of 5HTP and 4NDz in aqueous phosphate buffer (pH 7) was found to reach near-completion in less than a minute, while an identical reaction of 4NDz with tyrosine did not show noticeable progress in this timeframe (FIG. 1C). However, at elevated concentrations of Tyr, slow formation of the coupling product was observed (FIG. 1C). Even though these observations indicate that 4NDz may be used to selectively label 5HTP in the presence of Tyr, its non-negligible reactivity towards the latter prompted us to explore less electrophilic diazonium compounds with attenuated reactivity.

Figure 10B:
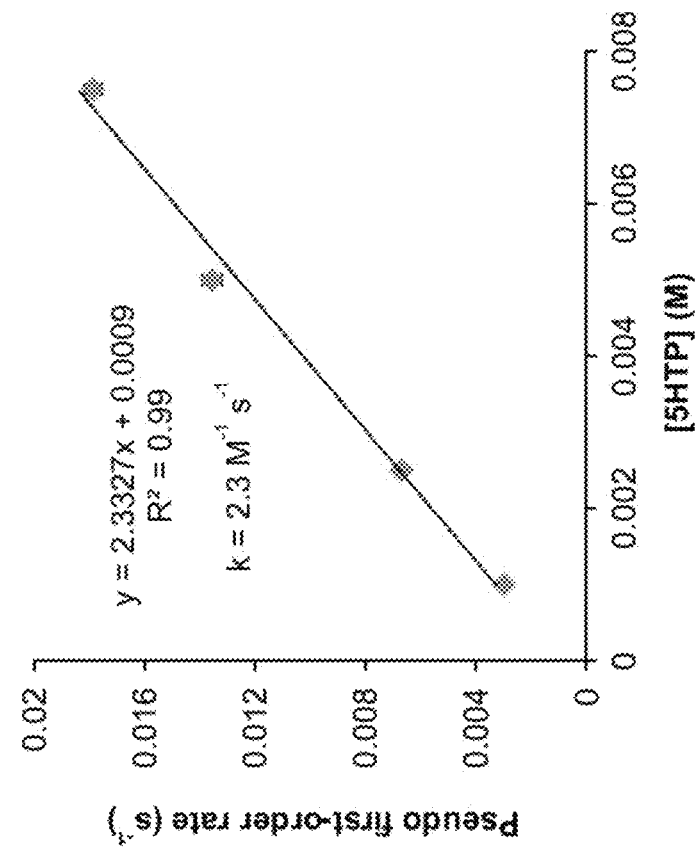
FIG. 10A-B shows evaluating the kinetic parameters of the reaction between 4MDz and 5HTP. Rate of product formation was measured under pseudo-first order conditions, where 10 µM 4MDz was mixed with an excess of 5HTP (1-8 nM) in 100 mM phosphate buffer at pH 7. A representative example is shown (A). The second-order rate constant was obtained by plotting the pseudo first-order rates against the concentration of 5HTP used (B). The reported value (2.3±0.1 $M^{-1}s^{-1}$) represents an average of three independent experiments; error represents standard deviation.
Figure 10A:
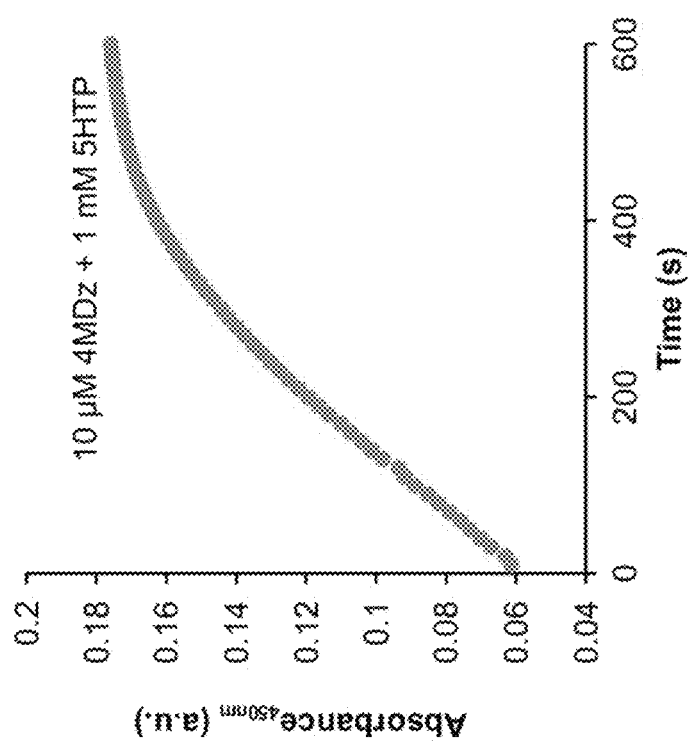
Figure 11:
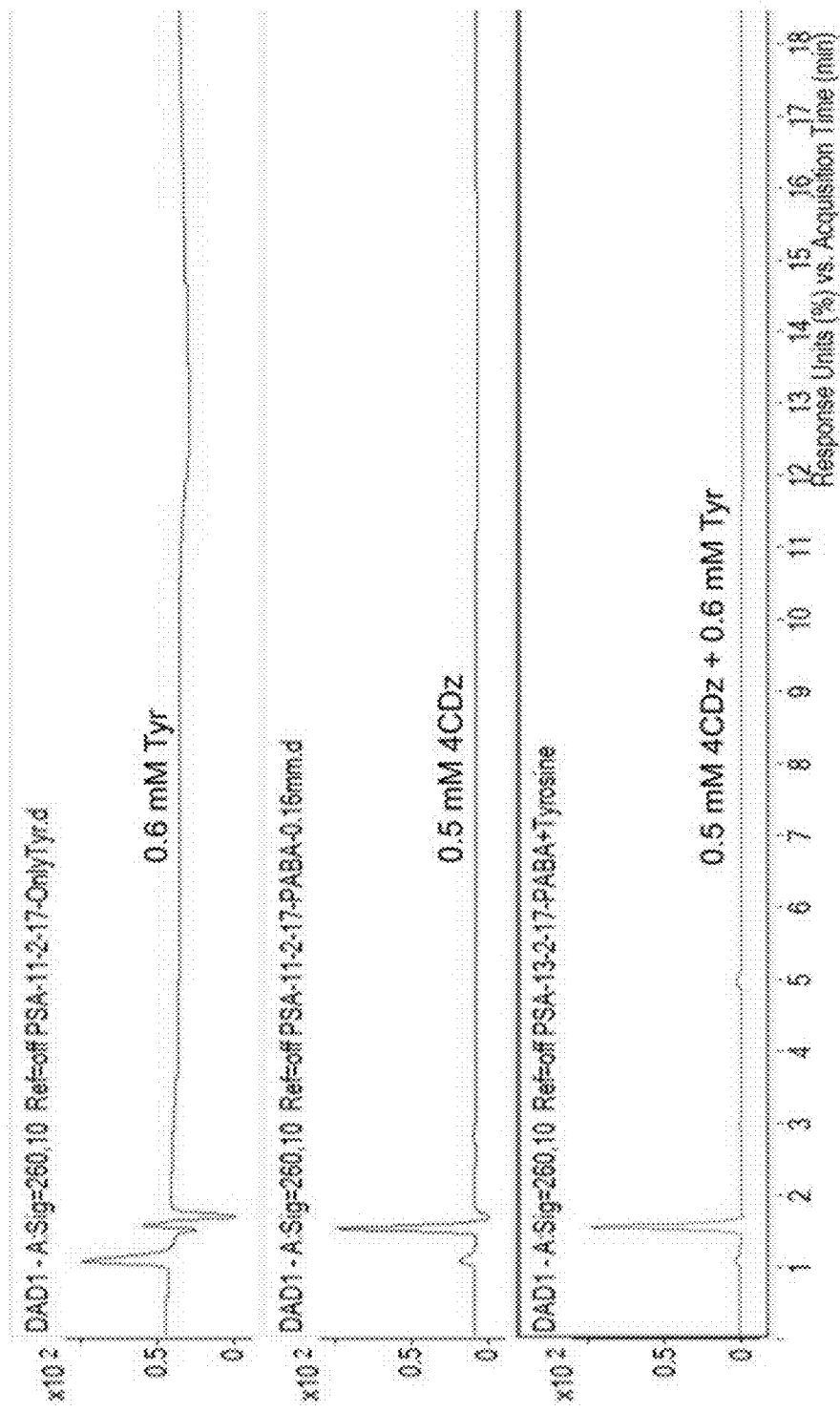
FIG. 11 shows HPLC-MS (ESI-TOF) analysis of a reaction between 4CDz (0.5 mM) with Tyr (0.6 mM) in 100 mM phosphate buffer (pH 7) show no formation of the azo-coupling product even after 30 min incubation (the product elutes at 14.5 min). Longer incubation leads to degradation of the diazonium.
Figure 13A:
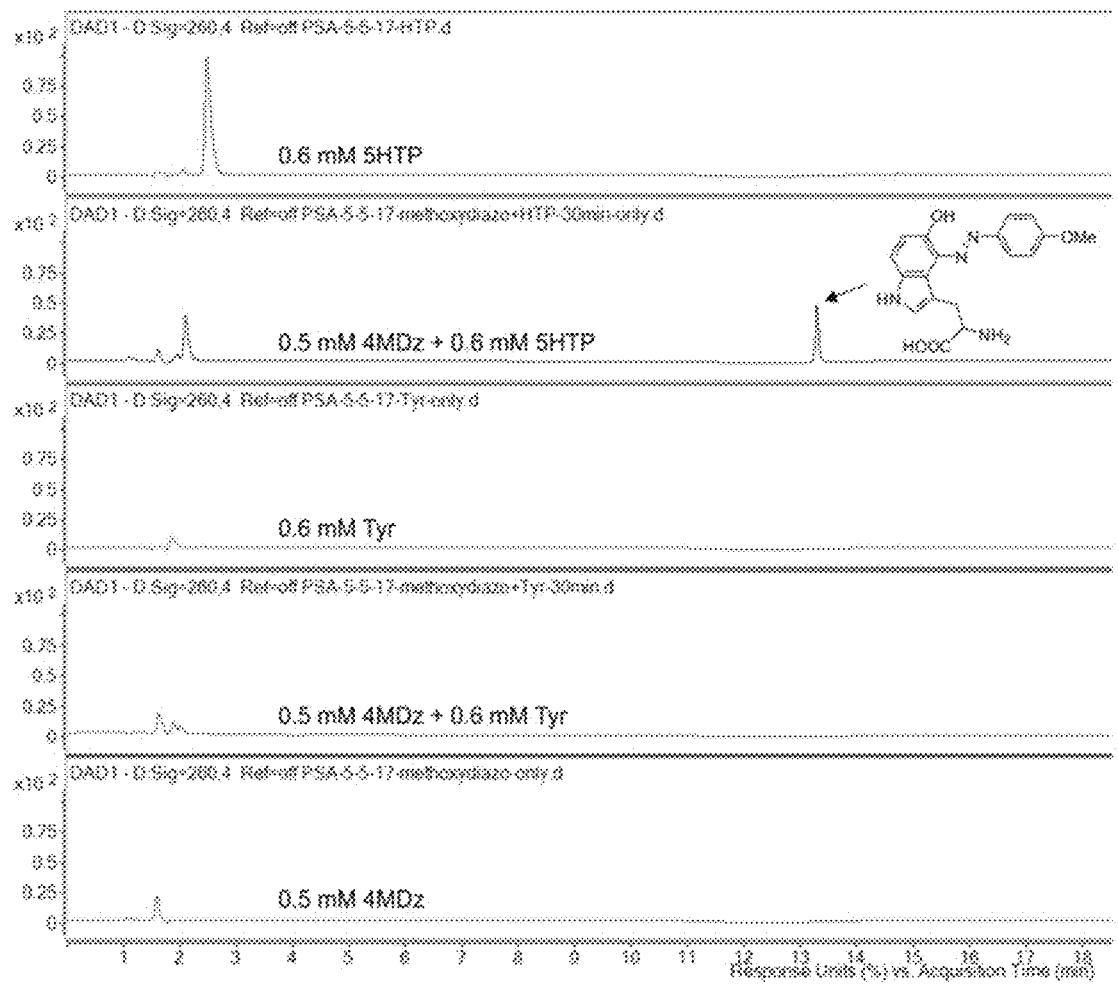
FIG. 13A-B shows HPLC-MS (ESI-TOF) analysis of the azo-coupling reactions of 4MDz with 5HTP and Tyr. Indicated reactions in 100 mM phosphate buffer (pH 7) were allowed to continue at room temperature for 30 minutes, and then analyzed by HPLC-MS. While formation of the azo-coupling product of 5HTP-4MDz was observed, no reaction was observed with Tyr. HPLC traces (A) and MS scans of the 5HTP-4MDz azo-coupling product peaks (B) are shown.
Figure 13B:
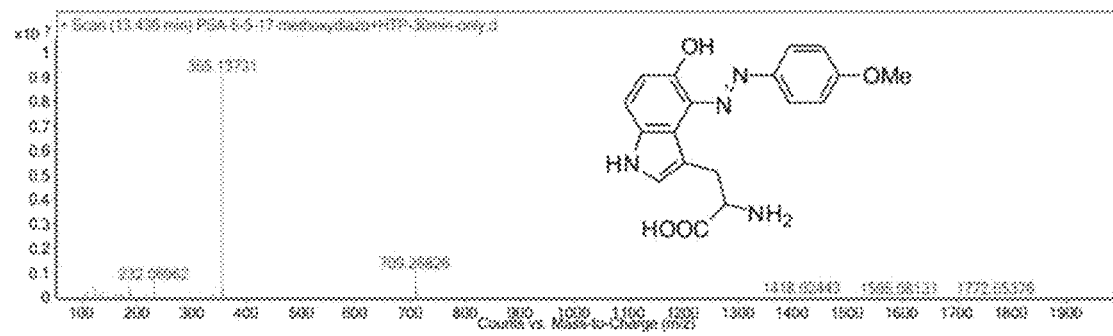
Figure 14:
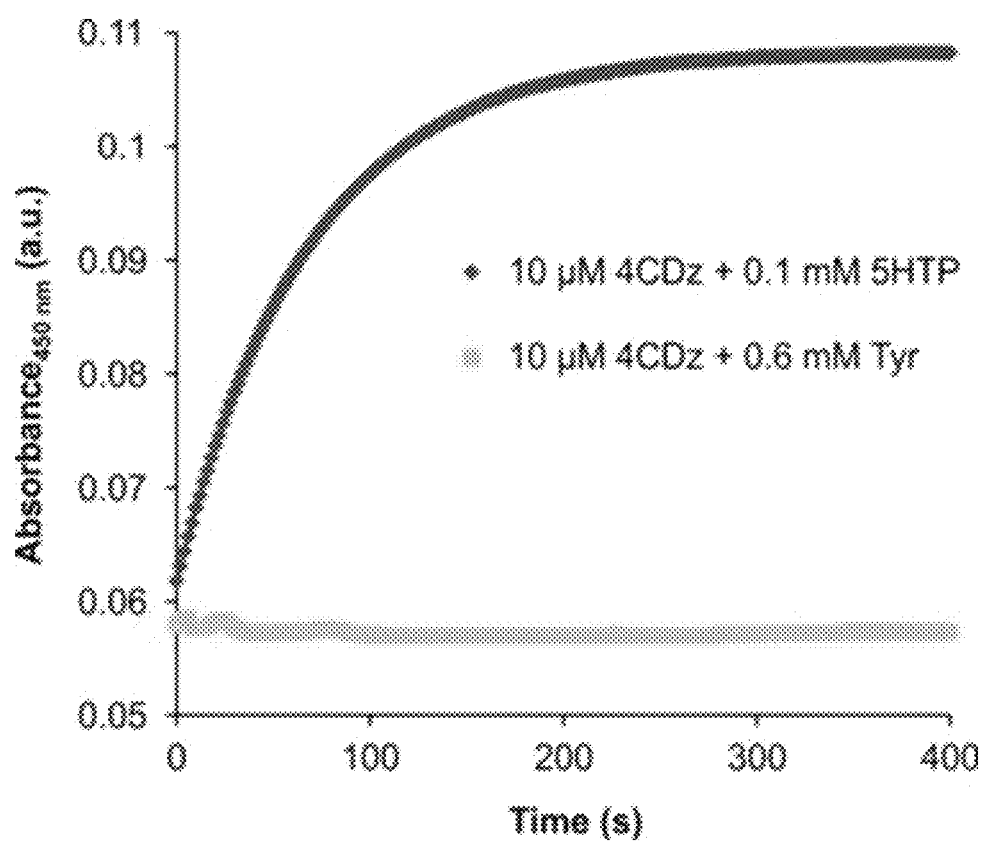
FIG. 14 shows 4CDz reacts selectively with 5HTP. When 10 µM 4CDz was reacted incubated with 0.1 mM of 5HTP in 100 mM phosphate buffer (pH 7), the reaction reached near completion in minutes, while the corresponding reaction with 0.6 nM Tyr showed no progress.
Figure 15:
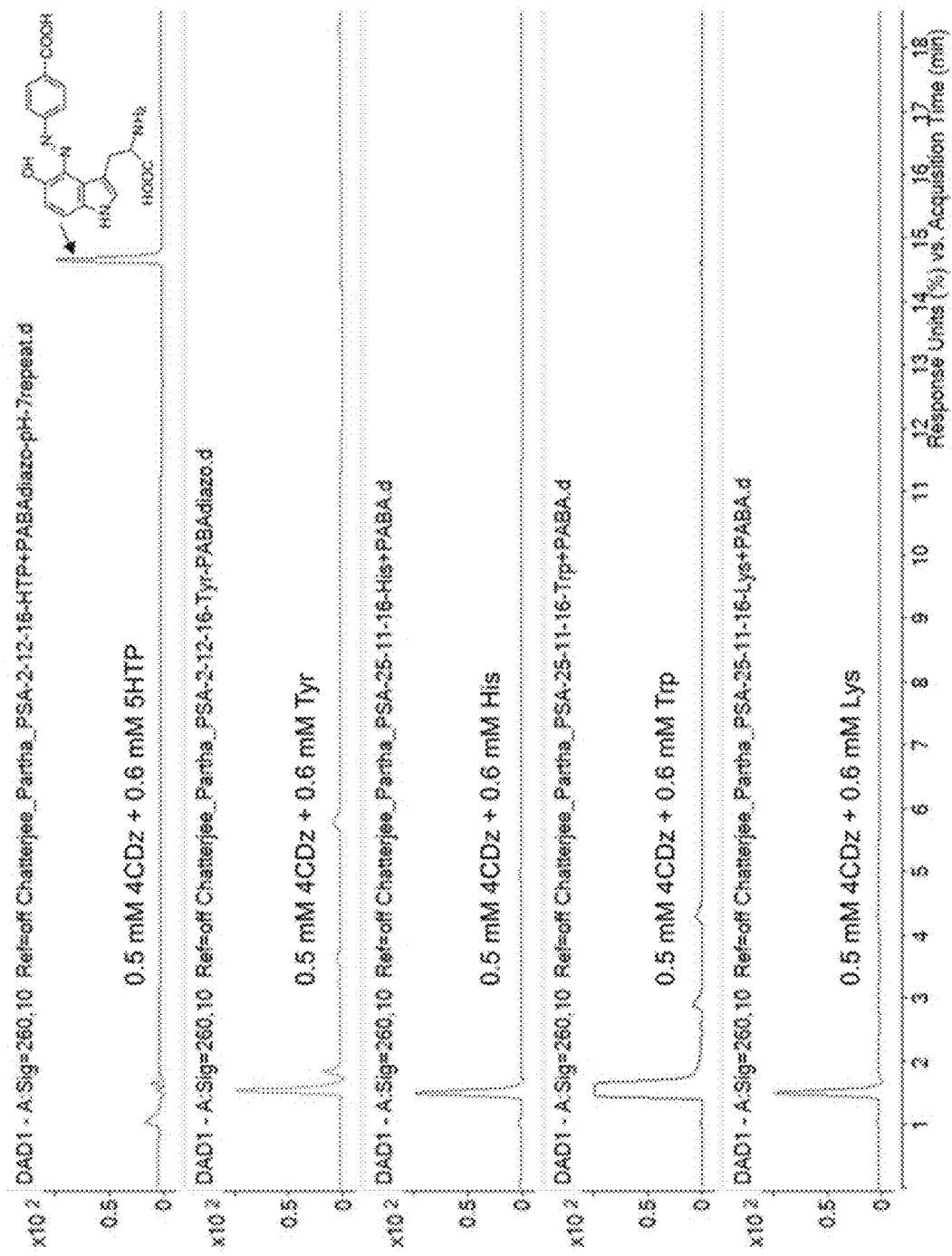
FIG. 15 shows HPLC-MS (ESI-TOF) analysis of the azo-coupling reactions of 4CDz with 5HTP and various canonical amino acids. Indicated reactions in 100 mM phosphate buffer (pH 7) were allowed to continue at room temperature for 30 minutes, and then analyzed by HPLC-MS. Only 5HTP was found to react with 4CDz under these conditions.

4-carboxybenzenediazonium (4CDz, 4) and 4-ethoxybenzenediazonium (4MDz, 5) were evaluated, which reacted with 5HTP with rate constants of 193±37 $M^{-1}s^{-1}$ (FIG. 1D) and 2.3±0.1 $M^{-1}s^{-1}$ (FIG. 10), respectively, but failed to react with tyrosine at pH 7, even after prolonged incubation (FIG. 11-13). Owing to its selective yet robust reactivity towards 5HTP, further studies were focused on the 4CDz scaffold. The reaction between 5HTP (0.1 mM) and 4CDz (10 μM) in 100 mM phosphate buffer (pH 7) was found to reach near-completion within minutes, while 4CDz failed to react with tyrosine and other canonical amino acids under similar conditions (FIG. 14-15). To characterize the product of the azo-coupling reaction with 5-hydroxyindole, three diazonium compounds were reacted with methyl 2-(5-hydroxy-1H-indol-3-yl)acetate (6; FIG. 2A), a 5HTP analog, and the resulting products were isolated and characterized by NMR ($^1$H and $^{13}$C) and mass-spectrometry. The product with 4MDz was also characterized by X-ray crystallography (FIG. 2B) to further confirm that the azo coupling occurs through the 4-position of the 5-hydroxyindole ring.

Figure 16:
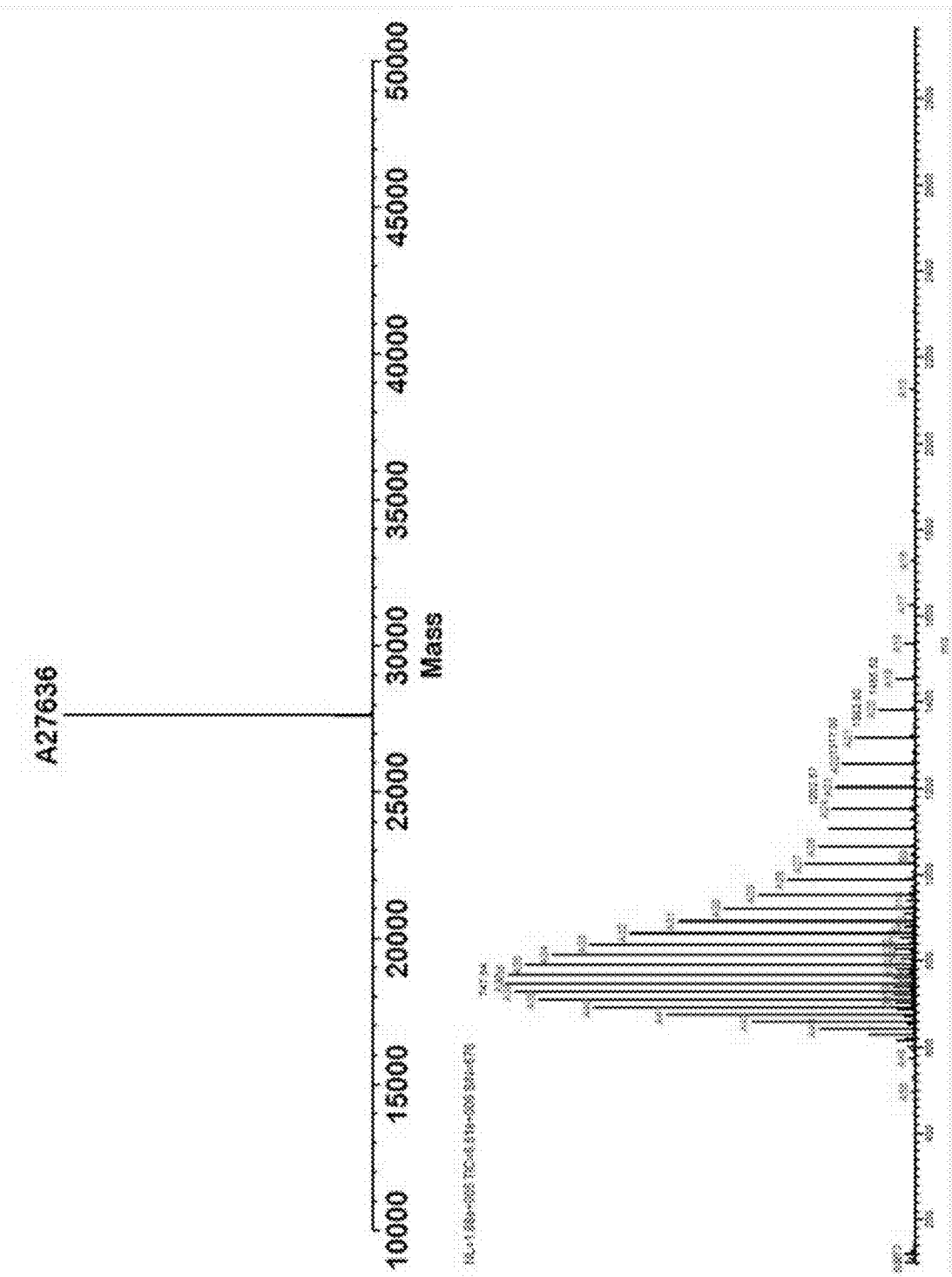
FIG. 16 shows ESI-MS analysis of sfGFP-151-5HTP expressed in ATM(Trp) *E. coli*. Bottom and top panel show raw and deconvoluted spectra, respectively. The observed mass matches expected mass (27636 Da).
Figure 17:
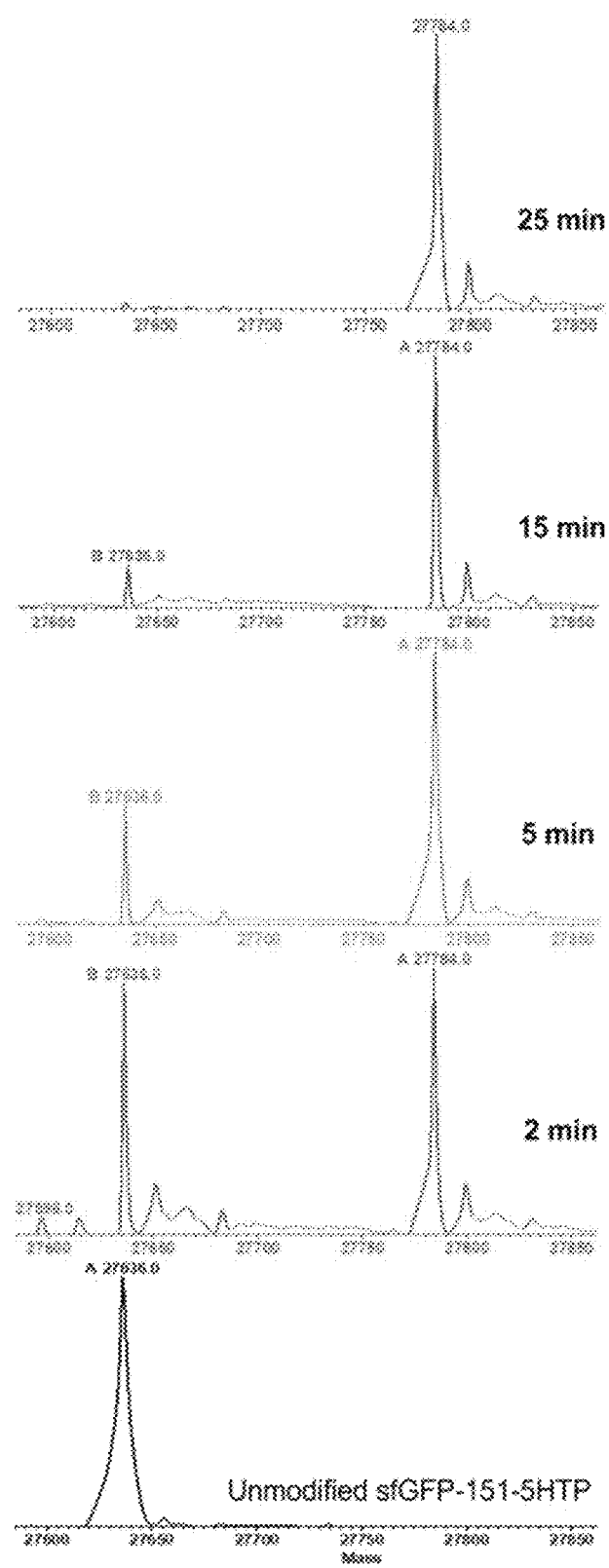
FIG. 17 shows rapid labeling of sfGFP-151-5HTP with 4CDz. A reaction between 10 µM sfGFP-151-5HTP and 40 µM 4CDz (at room temperature; in 100 mM phosphate buffer, pH 7) was quenched at different time points by adding excess 5HTP and the degree of protein labeling (expected mass 27784 Da) was monitored by ESI-MS over time.
Figure 18A:
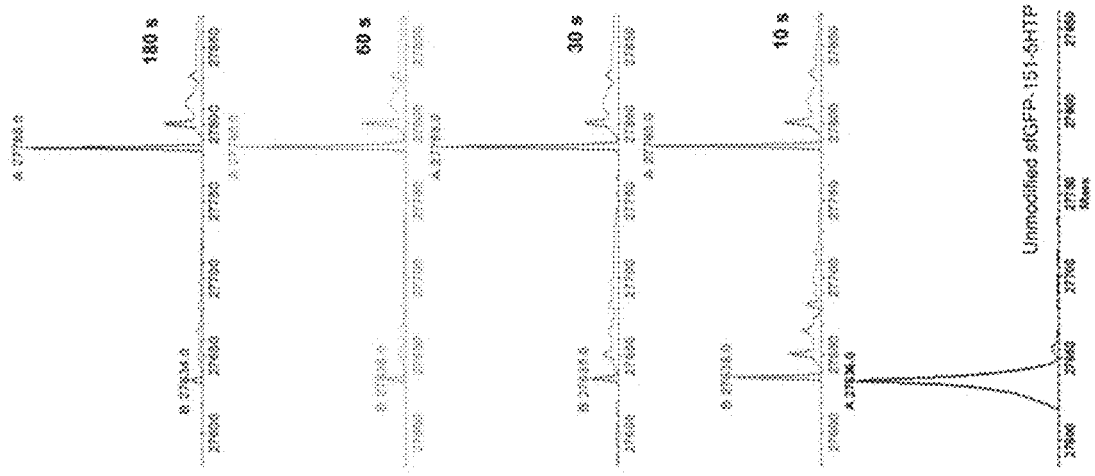
FIG. 18A-C shows A) when sfGFP-151-5HTP (10 µM) was incubated with 40 µM 4NDz in 100 mM phosphate buffer (pH 7) at room temperature, complete labeling (expected mass 27785 Da) was observed in minutes. B) identical treatment of wild-type sfGFP resulted in no protein modification. C) the reaction between sfGFP-151-5HTP and 5HTP was quenched with excess 5HTP at different points of time and degree of protein modification was monitored by ESI-MS.
Figure 18B:
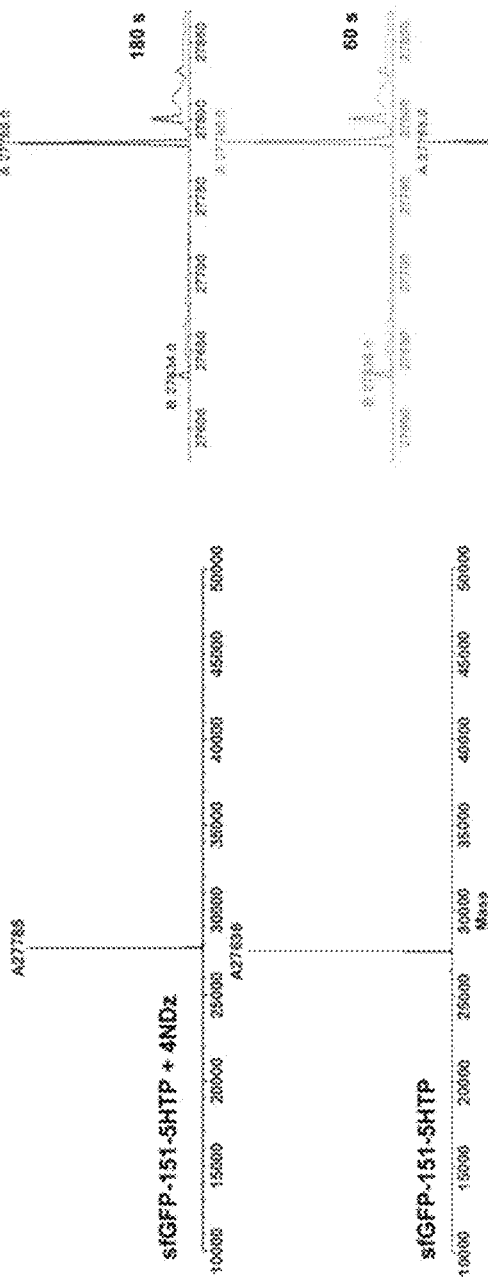
Figure 18C:
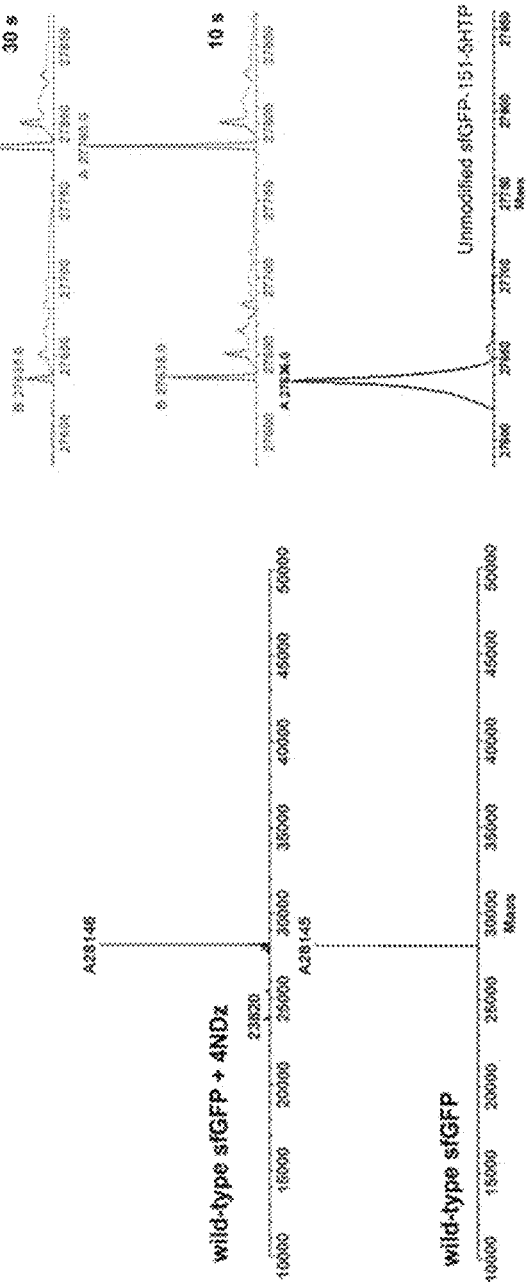
Figure 19:
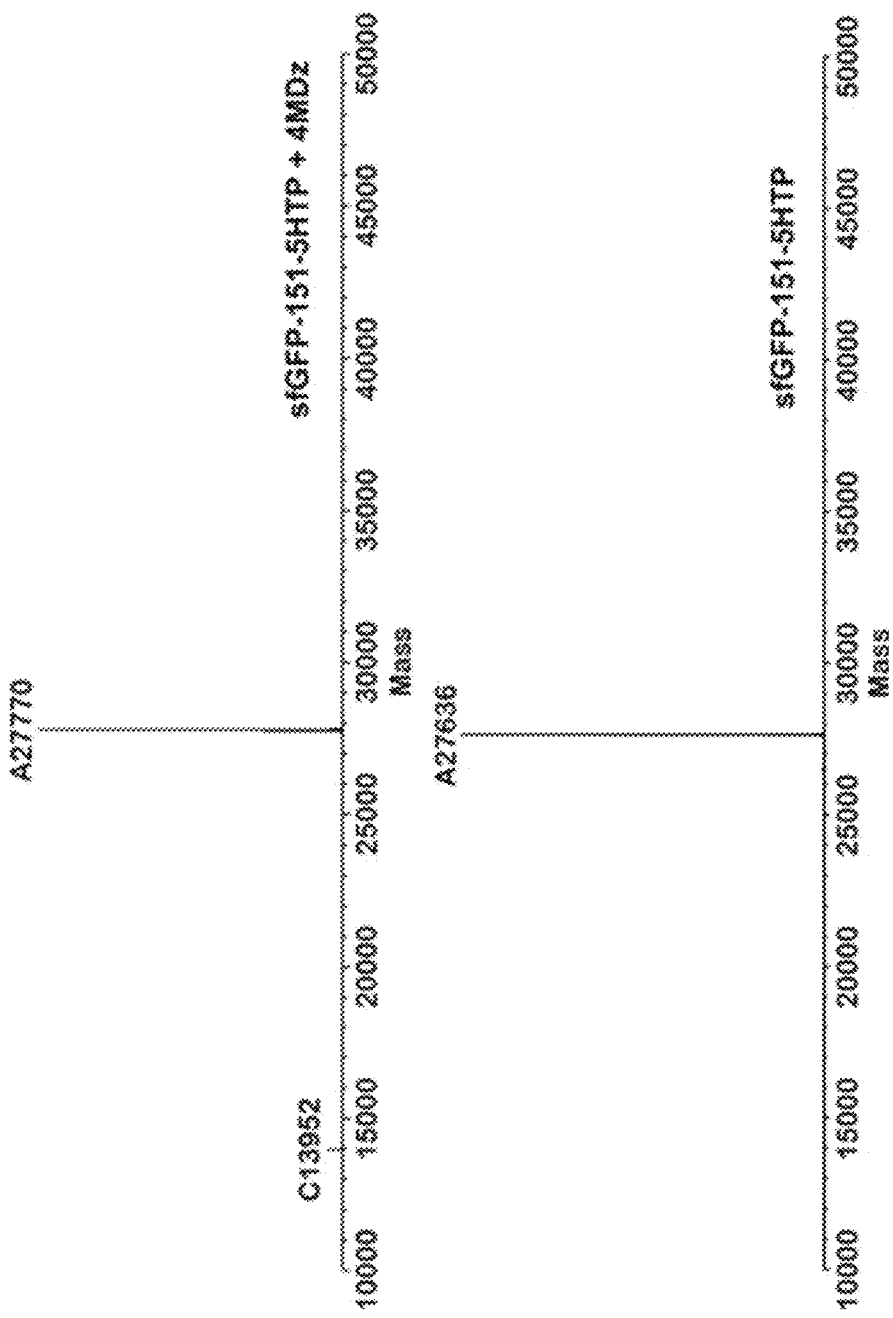
FIG. 19 shows when sfGFP-151-5HTP (10 µM) was incubated with 250 µM 4MDz in 100 mM phosphate buffer (pH 7) at room temperature, complete labeling (expected mass 27770 Da) was observed within 45 minutes.

The E. coli tryptophanyl-tRNA synthetase (EcTrpRS)/tRNA. pair was recently engineered to efficiently charge 5HTP in response to the TGA nonsense codon in both eukaryotes, as well as in an engineered E. coli strain, where the endogenous EcTrpRS/tRNATrp pair was functionally replaced with a eukaryotic counterpart. Using this platform, super-folder green fluorescent protein incorporating 5HTP at a permissive surface exposed site (sfGFP-151-5HTP; FIG. 16) was expressed. Incubation of sfGFP-151-5HTP with 40 μM 4CDz: resulted in its rapid and complete covalent modification (FIG. 3A, FIG. 17) within 30 min, as observed by mass-spectrometry analysis, while a nearly identical wild-type sfGFP (Tyr at 151 position) protein remained unmodified upon the same treatment (FIG. 3B). It was further showed that sfGFP-151-5HTP, but not wild-type sfGFP, can also be selectively modified using 4NDz (FIGS. 18) and 4MDz (FIG. 19). As expected, the labeling with 4NDz was significantly faster, reaching near-completion within a minute (FIG. 18C). These observations confirm that the genetically encoded 5HTP residue can be used to site-specifically label proteins using the chemoselective rapid azo-coupling reaction (CRACR).

Figure 20A:
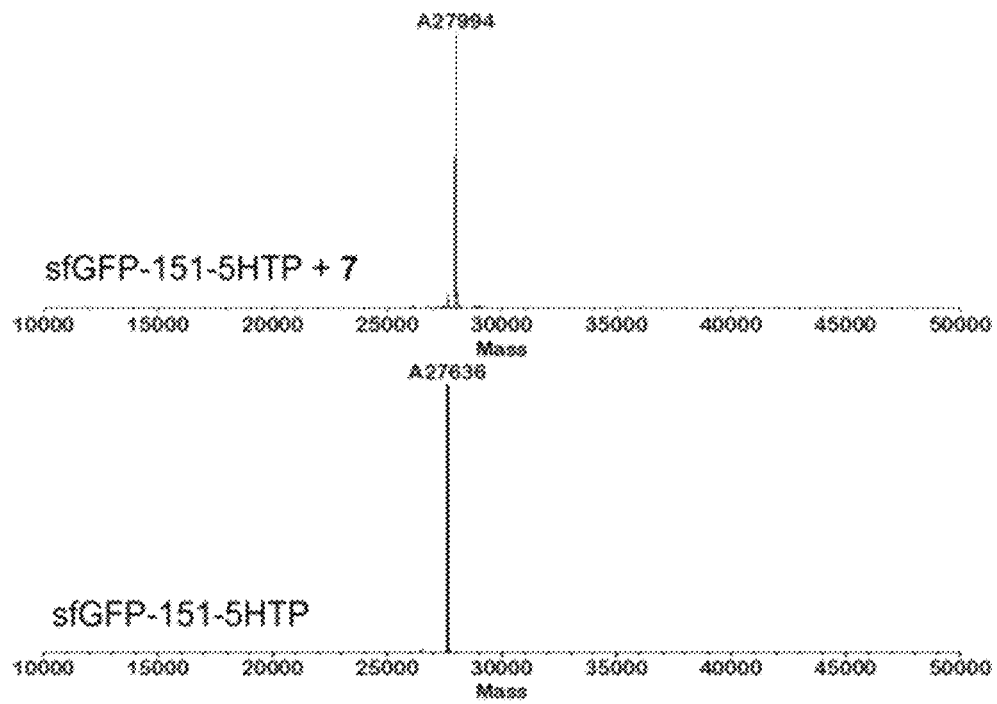
FIG. 20A-B shows A) treatment of sfGFP-151-5HTP (10 µM) with 150µM 7 (FIG. 3C) in 100 mM phosphate buffer (pH 7) on ice, resulted in complete labeling (expected mass 27994 Da). B) identical treatment of wild-type sfGFP resulted in no protein modification.
Figure 20:
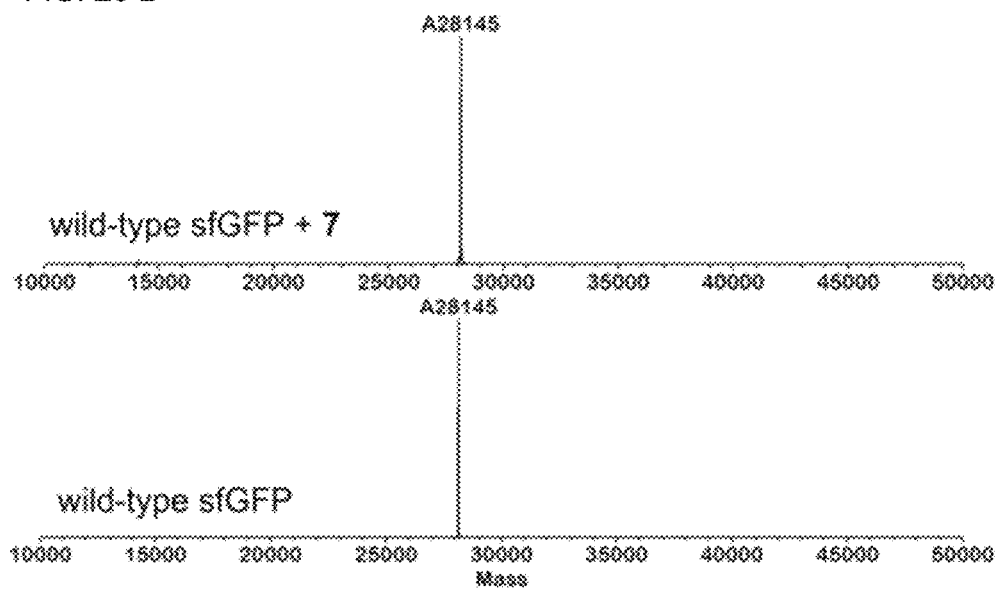
Figure 21A:
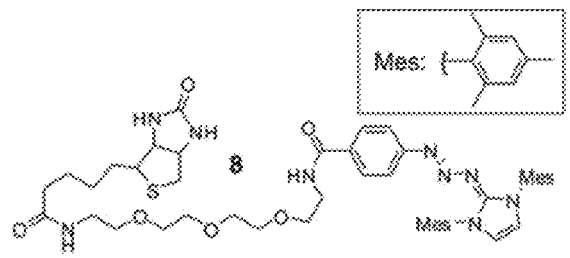
FIG. 21A-C shows A) the biotin-triazabutadiene conjugate can be rapidly photolyzed to release the biotin-4CDz conjugate, as shown previously. B) treatment of sfGFP-151-5HTP (10 µM) with 150 µM photolyzed 8 in 100 mM phosphate buffer (pH 7) on ice, results in complete labeling (expected mass 28184 Da). C) identical treatment of wild-type sfGFP resulted in no protein modification.
Figure 21B:
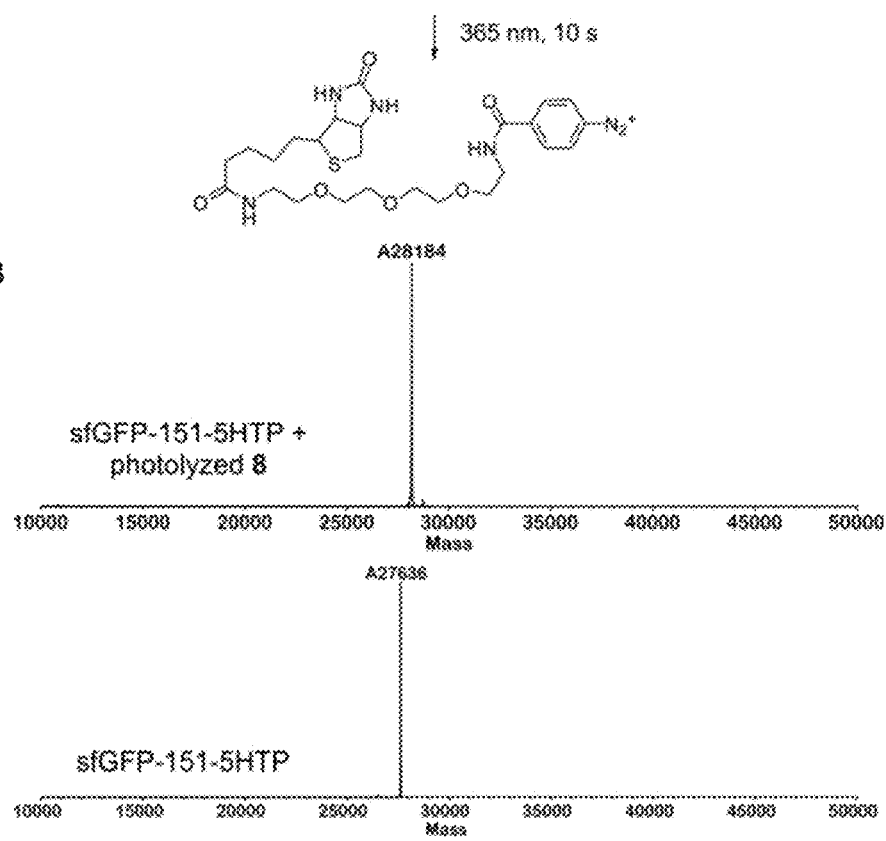
Figure 21C:
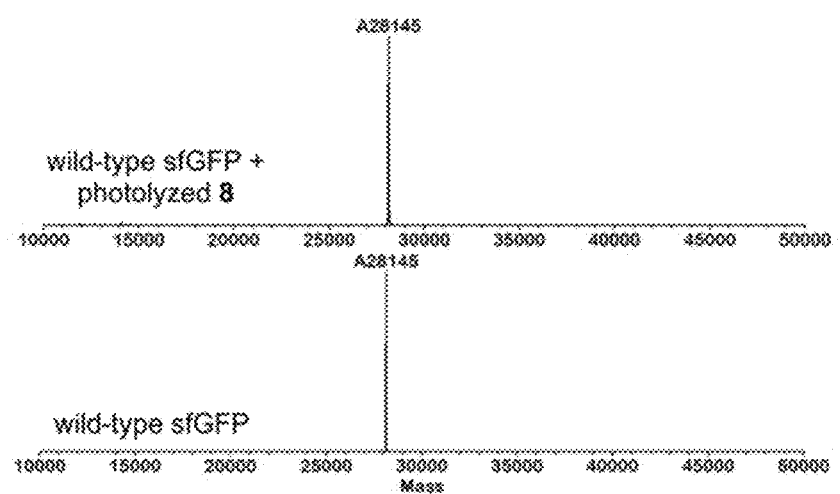

A fluorescent diazonium compound 7 (FIG. 3C) was generated from 6-aminofluorescein, which retains the 4CDz scaffold. Incubation with 7 resulted in selective and complete labeling of sfGFP-151-5HTP, but not wild-type sfGFP, as monitored by SDS-PAGE followed by fluorescence imaging (FIG. 3D), and mass-spectrometry (FIG. 20). Recently, the aryl-trizabutadiene group has been established to be a facile precursor to the aryl-diazonium species, the release of which can be triggered by light or low pH. A conjugate (8, FIG. 3C) was synthesized between biotin and a triazabutadiene, which upon brief irradiation releases biotin-4CDz (FIG. 21A). Selective biotinylation of sfGFP-151-5HTP was shown, but not wild-type sfGFP, upon treatment with biotin-4CDz by a western-blot analysis using a streptavidin-HRP probe (FIG. 3E), and MS analysis (FIG. 21).

Figure 4B:
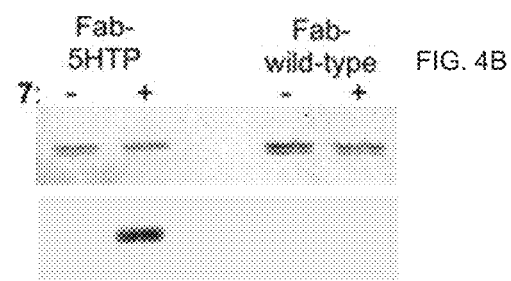
Figure 4C:
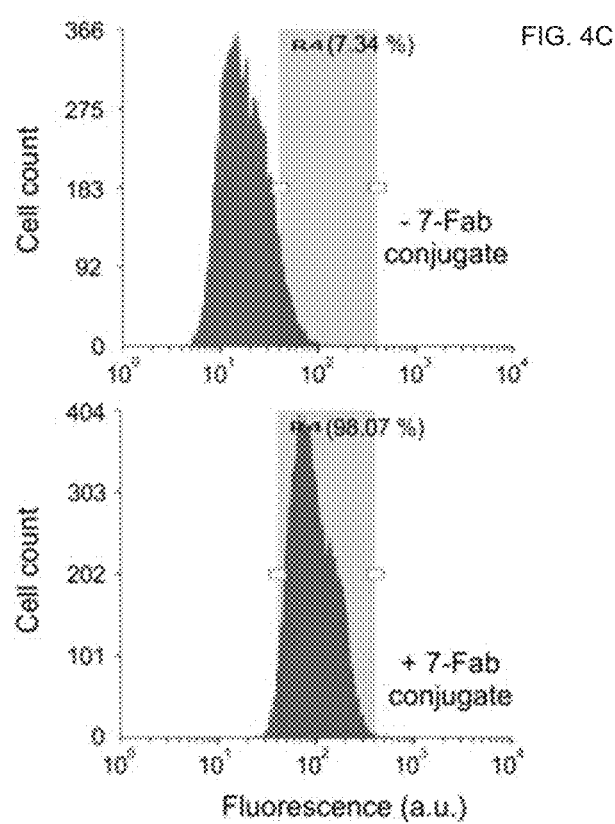

The ability to site-specifically label antibodies has been a valuable technology to generate therapeutically important antibody-drug conjugates, as well as covalent conjugates with biophysical probes that are important as diagnostics as well as research tools. To evaluate if CRACR can be used to generate such antibody-conjugates in a site-specific manner, the previously described Fab fragment of the anti-Her2 antibody Herceptin was expressed in the engineered E. coli strain, site-specifically incorporating 5HTP at position 169. The wild-type Fab protein was also expressed as a control (lysine at position 169). SDS-PAGE and ESI-MS analysis was used to confirm successful expression of both proteins (FIG. 4A-B). 80 μM of the fluorescent diazonium compound 7 was incubated with both the wild-type and the 5HTP-mutant anti-Her2 Fab for 15 min on ice. Subsequent ESI-MS analysis and SDS-PAGE, followed by fluorescence imaging, confirmed complete labeling of the 5HTP-mutant and no labeling of the wild-type antibody (FIG. 4A-B). The resulting fluorescently labeled antibody was dialyzed to remove the unreacted fluorophore, and was shown by fluorescence-activated cell sorting (FACS) analysis to successfully bind to the SK-BR-3 breast cancer cells, which overexpresses the Her2 receptor (FIG. 4C).

Figure 5A:
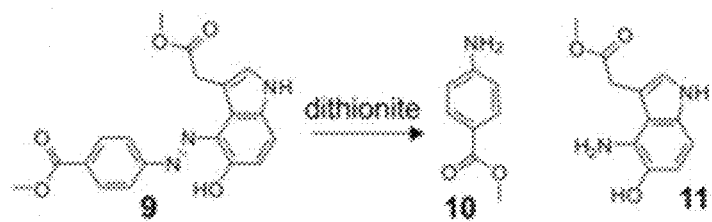
FIG. 5A-C shows the azo-linkage created through 5HTP-directed CRACR can be selectively cleaved using dithionite. A) Dithionite-mediated cleavage of the model azo-compound 9. B) HPLC-MS analysis of this reaction shows the production of the expected products (also see FIG. 22). C) Dithionite-mediated cleavage of the conjugate between photolyzed 8 and sfGFP-151-5HTP monitored by SDS-PAGE followed by coomassie staining and western blot (Streptavidin-HRP). Treating sfGFP-151-5HTP (left lane) with photolyzed 8 leads to its biotinylation (middle lane). Subsequent treatment of this purified conjugate with dithionite leads to the loss of the biotin group (right lane).
Figure 5B:
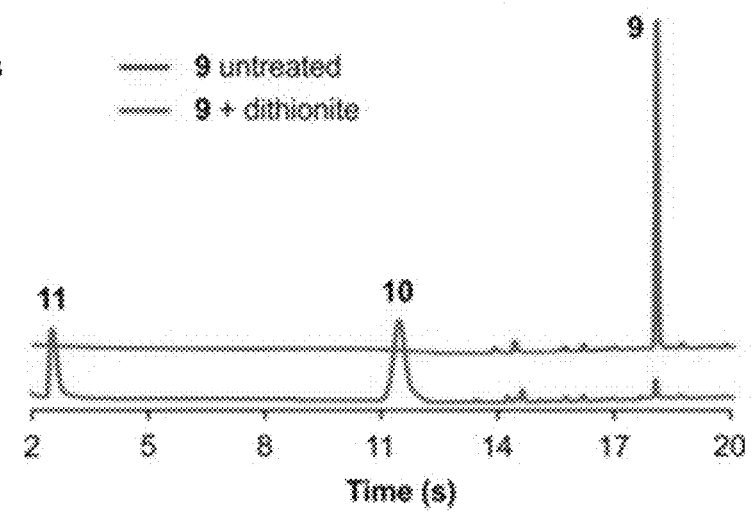
Figure 5C:
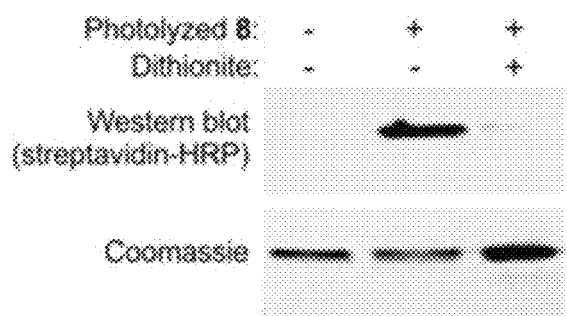
Figure 22:
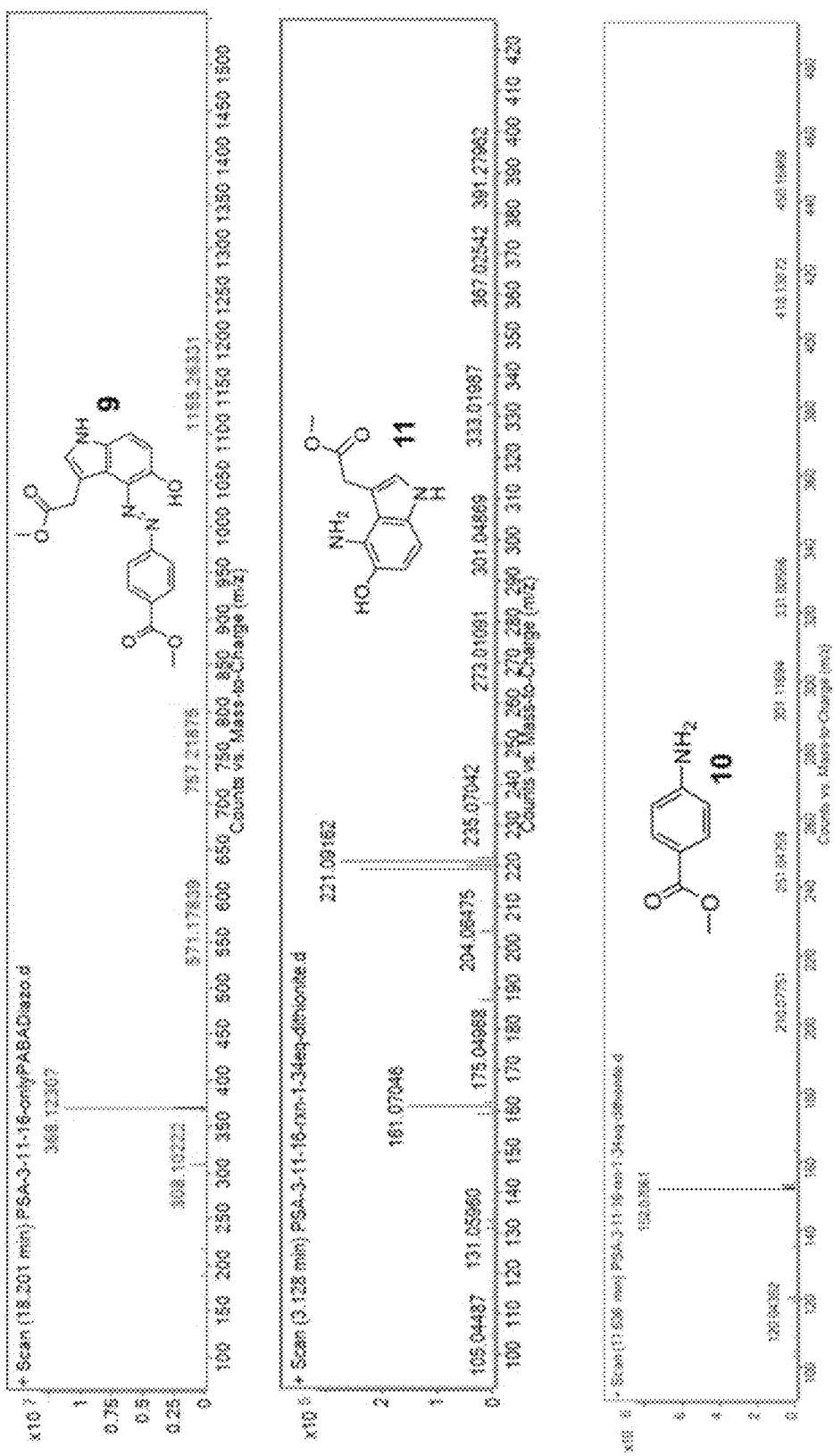
FIG. 22 shows MS scans of the peaks found in the HPLC analysis described in FIG. 5A confirms the dithionite mediated cleavage of 9 to 10 and 11.

Even though the azo-linkage is stable under physiologically relevant conditions, it is known to undergo facile cleavage upon treatment with dithionite, a strong but protein-compatible reducing agent. Given that the linkages generated by most available bioconjugation reactions are challenging to selectively undo under mild conditions, the present invention aimed to explore if the conjugate made through CRACR can be "unclicked" upon a dithionite treatment. Indeed, treatment of the purified model azo molecule 9 (FIG. 5A) with 1.5 mM dithionite led to its rapid reductive cleavage, as observed by HPLC-coupled MS analysis (FIG. 5A, FIG. 22). To demonstrate that the azo-linkage generated on a protein through a 5HTP residue can also be cleaved this way, the aforementioned conjugate (FIG. 3E) between sfGFP-151-5HTP and biotin-4CDz 8 was treated with dithionite and confirmed the removal of the biotin by a western-blot analysis (FIG. 5B). The remarkable speed and selectivity of the 5HTP-directed CRACR, and the ability to subsequently cleave the resulting azo-linkage, underscores unique advantages of this bioconjugation strategy.

While this invention has been particularly shown and described with references to preferred embodiments thereof, it will be understood by those skilled in the art that various changes in form and details may be made therein without departing from the scope of the invention encompassed by the appended claims.

What is claimed is:

1. A chemoselectively modified biomolecular conjugate comprising a protein, polypeptide or a peptide comprising naturally-occurring amino acids and one, or more, non-naturally-occurring amino acids comprising a surface-exposed 5-hydroxytryptophan or a 5-aminotryptophan moiety incorporated into the protein, polypeptide or peptide, wherein the non-naturally-occurring amino acid comprising the 5-hydroxytryptophan or the 5-aminotryptophan is chemoselectively modified over the naturally-occurring amino acids of the biomolecule, wherein the 5-hydroxytryptophan or the 5-aminotroptophan is covalently coupled to an aryl-diazonium compound selected from the group consisting of: 4-nitorbenzenediazonium (4NDz); 4-carboxybenzenediazonium (4NCDz) or 4-methoxvhenzenediazonium (4MCDz).

2. The conjugate of claim 1, wherein the protein is an antibody, or an antibody fragment.

3. The conjugate of claim 2, wherein the antibody fragment is an Fab fragment.

4. The conjugate of claim 1, wherein the aryl-diazonium compound is detectably labeled.

5. The conjugate of claim 4, wherein the label of the aryl-diazonium compound is selected from the group consisting of: a dye; a fluorophore; biotin or a radioisotope.

6. The conjugate of claim 1, wherein the aryl-diazonium compound is modified with or linked to a small organic molecule, a therapeutic drug, polyethylene glycol, a nucleic acid, a protein, a polypeptide, a peptide or a biophysical probe.

7. The conjugate of claim 1, wherein the aryl-diazonium compound is immobilized on a solid matrix, surface or support.

8. The conjugate of claim 7, wherein the solid support is a bead.

9. The conjugate of claim 1, wherein the covalent coupling between the 5-hydroxyindole groups or the 5-aminoindole groups and the diazonium compound is cleavable with a suitable reducing agent.

10. The conjugate of claim 9, wherein the reducing agent is dithionite.

11. A chemoselectively labeled antibody conjugate, or antibody fragment conjugate, wherein the antibody, or antibody fragment comprises naturally-occurring amino acids and one, or more, non-naturally-occurring amino acids comprising a surface-exposed 5-hydroxytryptophan or a 5-aminotryptophan moiety incorporated into the antibody, wherein the non-naturally-occurring amino acid comprising 5-hydroxytryptophan or the 5-aminotryptophan is chemoselectively modified over the naturally-occurring amino acids of the biomolecule, wherein 5-hydroxytryptophan or the 5-aminotryptophan is covalently coupled to a detectably-labeled aryl-diazonium compound selected from the group consisting of: 4-nitrobenzenediazonium (4NDz); 4-carboxybenzenediazonium (4NCDz) or 4-methoxybenzenediazonium (4MCDz).

12. The conjugate of claim 11, wherein the antibody fragment is an Fab fragment.

13. The conjugate of claim 12, wherein the Fab fragment is an Fab fragment of the anti-Her2antibody Herceptin.

14. The conjugate of claim 11, wherein the label is a fluorescent label.

15. A kit comprising the biomolecular conjugate of claim 1, wherein the conjugate is detectably labeled.

16. The kit of claim 15, wherein the biomolecule is an antibody, or antibody fragment.

17. The biomolecular conjugate of claim 1, wherein the diazonium compound is conjugated to the 5-hydroxytryptophan or the 5-aminotryptophn at the C4position.

18. The biomolecular conjugate of claim 1, wherein the protein is sfGFP and the 5-hydroxytryptophan or 5-aminotryptophan is located at position 151 of the protein.

19. The biomolecular conjugate of claim 11, wherein the antibody is the Fab fragment of the anti-Her2 antibody and the 5-hydoxytryptophan or 5- aminotryptophan is located at position 169 of the antibody.

* * * * *

UNITED STATES PATENT AND TRADEMARK OFFICE
CERTIFICATE OF CORRECTION

PATENT NO. : 11,890,351 B2
APPLICATION NO. : 16/012060
DATED : February 6, 2024
INVENTOR(S) : Abhishek Chatterjee et al.

It is certified that error appears in the above-identified patent and that said Letters Patent is hereby corrected as shown below:

In the Specification

Column 1, Line 30, delete "Aider" and insert -- Alder --

Column 2, Line 46, delete "(4NCDz) and insert -- (4CDz) --

Column 6, Line 58, delete "(1-8 nM)" and insert -- (1-8 mM) --

Column 7, Line 22, delete "0.6nM" and insert -- 0.6mM --

Column 8, Line 21, delete "liked" and insert -- listed --

Column 11, Line 28, delete "(4MDz)" and insert -- (4CDz) --

Column 12, Line 32, delete "(4NDz-SHIP)" and insert -- (4NDz-5HTP) --

Column 13, Line 3, delete "MCl" and insert -- HCl --

Column 15, Line 43, delete "4-ethoxyben-" and insert -- methoxyben- --

In the Claims

Claim 1, Column 17, Line 30, delete "4NCDz" and insert -- 4CDz --

Claim 1, Column 17, Line 30, delete "4MCDz" and insert -- 4MDz --

Claim 1, Column 17, Line 30, delete "methoxvhenzenediazonium" and insert -- methoxybenzenediazonium --

Claim 11, Column 18, Line 23, delete "4NCDz" and insert -- 4CDz --

Signed and Sealed this
Third Day of September, 2024

Katherine Kelly Vidal
*Director of the United States Patent and Trademark Office*

CERTIFICATE OF CORRECTION (continued)
U.S. Pat. No. 11,890,351 B2

Claim 11, Column 18, Line 24, delete "4MCDz" and insert -- 4MDz --

Claim 17, Column 18, Line 38, delete "5-aminotryptophn" and insert -- 5-aminotryptophan --